US010906180B1

(12) United States Patent
 Chefitz

(10) Patent No.: US 10,906,180 B1
(45) Date of Patent: Feb. 2, 2021

(54) MONITORING AND MAINTAINING AN INTRAVENOUS ASSEMBLY WITHOUT MEDICAL STAFF INVOLVEMENT FOR SAFE DISTANCING ENFORCEMENT

(71) Applicant: 123IV, Inc., New Rochelle, NY (US)

(72) Inventor: Allen B. Chefitz, New Rochelle, NY (US)

(73) Assignee: 123IV, Inc., New Rochelle, NY (US)

( * ) Notice: Subject to any disclaimer, the term of this patent is extended or adjusted under 35 U.S.C. 154(b) by 0 days.

(21) Appl. No.: 16/880,789

(22) Filed: May 21, 2020

Related U.S. Application Data

(63) Continuation-in-part of application No. 16/776,826, filed on Jan. 30, 2020.

(51) Int. Cl.
  *B25J 9/16*  (2006.01)
  *B25J 11/00* (2006.01)
  *B25J 9/00*  (2006.01)
  *A61M 5/142* (2006.01)
  *A61M 5/168* (2006.01)

(52) U.S. Cl.
  CPC .......... *B25J 9/1674* (2013.01); *A61M 5/142* (2013.01); *A61M 5/16831* (2013.01);
  (Continued)

(58) Field of Classification Search
  CPC ........ A61M 5/16831; A61M 2202/202; A61M 2005/16863; A61M 5/1685; A61M 5/16;
  (Continued)

(56) References Cited

U.S. PATENT DOCUMENTS 9,216,243 B2  12/2015  Millman et al.
9,272,092 B2   3/2016  Aguerre et al.
(Continued)

FOREIGN PATENT DOCUMENTS

CN   203029630 A   7/2013
CN   103482863 A   1/2014
(Continued)

OTHER PUBLICATIONS

Chan, Jasper Fuk-Woo, et al. "A Familial Cluster of Pneumonia Associated with the 2019 Novel Coronavirus Indicating Person-to-Person Transmission: a Study of a Family Cluster.", Jan. 24, 2020, The Lancet, vol. 395, No. 10223, pp. 514-523., doi: 10.1016/s0140-6736(20)30154-9. (Year: 2020).*

*Primary Examiner* — Kevin C Sirmons
*Assistant Examiner* — Tezita Z Watts
(74) *Attorney, Agent, or Firm* — David H. Judson

(57) ABSTRACT

A method and system to monitor and autonomously configure an intravascular assembly without medical staff involvement or presence. In this solution, a robotic device is associated with an intravascular assembly, which has tubing through which fluids are delivered intravenously. Monitoring of the tubing is initiated. In response to the monitoring, an errant flow through the tubing is detected; typically, the errant flow results from one of: a kink or twist in the tubing, an air bubble in the tubing, an occlusion or clot in the tubing, and pressure variations. In response to detecting the errant flow, and in advance of an audible alarm being generated in association with the intravascular assembly, a command is then issued to the associated robotic device. The command is configured to initiate, by the robotic device, physical engagement with and mechanical manipulation of the tubing, thereby remediating the errant flow automatically.

11 Claims, 29 Drawing Sheets

(52) U.S. Cl.
CPC ............ *B25J 9/0006* (2013.01); *B25J 9/1664* (2013.01); *B25J 11/009* (2013.01); *A61M 2005/16863* (2013.01); *A61M 2202/206* (2013.01); *A61M 2205/18* (2013.01); *A61M 2205/3303* (2013.01)

(58) Field of Classification Search
CPC ........ A61M 5/142; A61B 34/70; A61B 34/00; B25J 9/1674; B25J 9/0003; B25J 9/0006; B25J 9/1664; B25J 11/009; B25J 9/00; B25J 11/00

See application file for complete search history.

(56) References Cited

U.S. PATENT DOCUMENTS

| | | | |
|---|---|---|---|
| 9,364,171 | B2 | 6/2016 | Harris et al. |
| 9,510,912 | B2 | 12/2016 | Bencteux et al. |
| 2005/0003340 | A1* | 1/2005 | Chou .................... C12Q 1/701 435/5 |
| 2012/0136325 | A1* | 5/2012 | Allen .................. A61M 1/0037 604/319 |
| 2012/0190981 | A1* | 7/2012 | Harris .............. A61B 5/150389 600/439 |
| 2013/0113871 | A1* | 5/2013 | Ballantyne ............. G16H 40/63 348/14.05 |
| 2016/0018347 | A1 | 1/2016 | Drbal et al. |
| 2017/0182244 | A1* | 6/2017 | Blomquist ........ A61M 5/16831 |
| 2018/0185099 | A1 | 7/2018 | Kottenstette et al. |

FOREIGN PATENT DOCUMENTS

| | | |
|---|---|---|
| CN | 104248790 A | 12/2014 |
| CN | 106880891 A | 6/2017 |
| KR | 101382856000 B | 4/2014 |

* cited by examiner

MONITORING AND MAINTAINING AN INTRAVENOUS ASSEMBLY WITHOUT MEDICAL STAFF INVOLVEMENT FOR SAFE DISTANCING ENFORCEMENT

BACKGROUND

It is common in the medical field to administer medications and other fluids to patients by intravenous infusion. During intravenous infusion, an intravenous assembly including an infusion pump is used to administer a prescribed amount of medication or fluids over a certain period of time. Infusion products are typically delivered to the patient in a clear, see-through plastic intravenous bag and dispensed through clear tubing hooked up to a catheter attachment. While intravenous infusion is implemented quite often, patients and medical staff can encounter multiple problems associated with components of the intravenous assembly during administration.

For example, infusion pump alarms can cause numerous issues for both patients and medical staff. Continuous alarms and delayed efforts of medical staff at correcting an error that triggered the alarm can cause sleep deprivation in a patient, which can affect a patient's ability to heal. Further, alarms triggered from roommate infusion pumps and/or when a patient is mobile with an infusion pump can also interfere with a patient's overall care.

The monitoring of infusion pumps as well as correcting triggered alarms can be time consuming for medical staff in a hospital. For example, depending on a nurse's schedule and workload, it can take up to thirty minutes or more for an infusion pump's alarm to be addressed. During this time, as the alarm continues to ring, intravenous tubing has a greater risk of clotting which can harm the patient.

Infusion pump alarms can be triggered for multiple reasons. For example, an alarm can be triggered when air bubbles are trapped in intravenous tubing from an intravenous bag being manually changed, occlusions occur from kinking or clots in the intravenous tubing, intravenous bags of fluids or medications become empty, and/or a pump has a low battery. Typically, medical staff can silence the alarm manually, can unkink kinked intravenous tubing, can manually flush intravenous tubing with saline solution to remove a clot, can disconnect intravenous tubing from the patient and flush the intravenous assembly of its air bubbles, can replace a finished intravenous bag with a new one, and/or can plug the intravenous pump into the wall outlet when a low battery is detected. However, the completion of these tasks can be delayed, time consuming and alarms will continue to ring until medical staff have finished these tasks.

An additional problem associated with the use of an intravenous assembly is the improper placement of sensors within components of the intravenous assembly that inaccurately detect causes of errant flow. For example, when sensors are located within intravenous tubing and/or catheters, these sensors are often not sensitive enough to properly detect air bubbles in the tubing and/or catheters due in part to the location of the sensors.

Therefore, it would be beneficial to provide a system and method for monitoring and maintaining an intravenous assembly autonomously without the need for medical staff involvement, thereby protecting the staff by enabling safe distancing from a patient (e.g., one experiencing active Covid-19 disease symptoms) where possible.

It would also be beneficial to provide a robotic device that preemptively maintains the intravenous system so that intravenous pump alarms are not triggered. Further, it would be beneficial to provide a robotic device that includes a robotic arm that can, among other things, unkink intravenous tubing, manually palpate air bubbles out of the intravenous tubing, replace an almost empty intravenous bag, flush an obstructed intravenous tubing of a clot, and/or with ultrasound guidance, insert new intravenous tubing and a catheter into a patient.

BRIEF SUMMARY

The present application provides a system for monitoring and maintaining an intravenous assembly autonomously without the need for medical staff involvement. The system includes a robotic device that corrects intravenous pump alarms as well as maintains the intravenous assembly by correcting or maintaining specific components of the intravenous assembly that trigger an alarm. The robotic device is capable of maintaining the intravenous system so that intravenous pump alarms are not triggered.

In one embodiment, a system for monitoring and maintaining an intravenous assembly is provided. The system comprises a robotic device. The robotic device includes an optical sensor configured to detect an errant flow in at least a component of the intravenous assembly, and a pressure sensor configured to manipulate at least the component of the intravenous assembly to restore, start, stop flow, or change at least the component of the intravenous assembly.

In some embodiments, an intravenous tubing is provided. The intravenous tubing comprises at least one sensor configured to communicate with and provide data to the robotic device described above. The at least one sensor is disposed at a proximal end or a distal end of the intravenous tubing.

In some embodiments, a catheter is provided. The catheter comprises at least one sensor disposed within an interior and/or exterior of the catheter. The at least one sensor is configured to communicate with and provide data to the robotic device described above.

In some embodiments, an intravenous container is provided. The intravenous container comprises an interior surface and an exterior surface. The interior surface and/or the exterior surface include at least one sensor configured to communicate with and provide data to the robotic device described above.

In some embodiments, an intravenous pump is provided. The intravenous pump comprises at least one sensor configured to communicate with and provide data to the robotic device described above.

Other features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

In part, other aspects, features, benefits and advantages of the embodiments will be apparent with regard to the following description, appended claims, and accompanying drawings in which:

Figure 1:
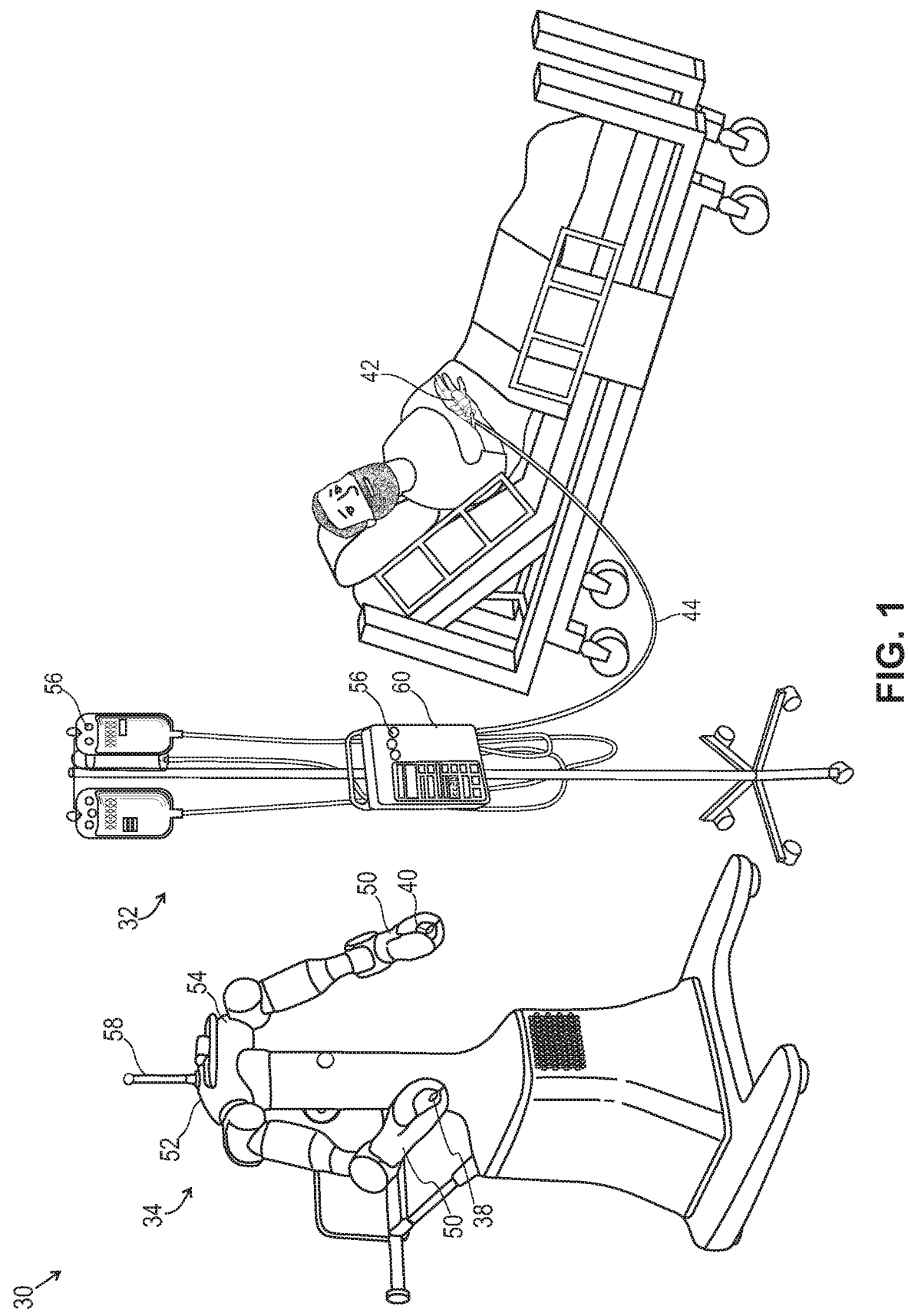
FIG. 1 is a perspective view of a system for monitoring and maintaining an intravenous assembly comprising a robotic device. The robotic device has an optical sensor configured to detect an errant flow in at least a component of the intravenous assembly and a pressure sensor configured to manipulate at least the component of the intravenous assembly to restore, start, stop flow, or change at least the component of the intravenous assembly. The robotic device is depicted as a humanoid robot and the patient is shown attached to the intravenous assembly.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under anyone heading may be used in conjunction with embodiments under any other heading.

DETAILED DESCRIPTION

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. The following description is presented to enable any person skilled in the art to make and use the present disclosure.

Notwithstanding that the numerical ranges and parameters setting forth the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

With regard to the following description, it is to be understood by those skilled in the art that unless a specific number of an introduced claim element is recited in the claim, such claim element is not limited to a certain number. For example, introduction of a claim element using the indefinite article "a" or "an" does not limit the claim to "one" of the element. Still further, the following appended claims can contain usage of the introductory phrases "at least one" and "one or more" to introduce claim elements. Such phrases are not considered to imply that the introduction of a claim element by the indefinite articles "a" or "an" limits any particular claim containing such introduced claim element to coverage of devices or processes containing only one such element or containing more than one such element, even when the same claim includes the introductory phrases "one or more" or "at least one."

It is to be further understood that claim terminology relating to elements A, B, and C recited as "one of A, B, and C" is intended to cover systems, devices or processes having one or more of element A, or one or more of element B, or one or more of element C, and does not require the presence of three of such elements A, B, and C, nor exclude coverage of systems, devices or processes including the presence of three of such elements A, B, and C. Likewise, recitation of "at least one of A, B, and C" is to be given the same interpretation. On the other hand, if it is intended to limit coverage of a claim to systems, devices or processes including one of each of a set of elements, the phraseology "one of each of A, B, and C" or "at least one of each of A, B, and C" is used.

Ranges may be expressed herein as from "about" or "approximately" one particular value and/or to "about" or "approximately" another particular value. When such a range is expressed, another embodiment includes from the one particular value and/or to the other particular value.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", or the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

As used herein, the terms "having," "containing," "including," "comprising," and the like are open ended terms that indicate the presence of stated elements or features, but do not preclude additional elements or features.

It is also to be further understood that the doctrine of claim differentiation is to be applied across an independent claim and its dependents and is not intended to be applied across a plurality of independent claims. For example, term A in a first independent claim may be interpreted to have the same scope as term B in second independent claim, while if term A is in a first independent claim and term B further defines term A in claim dependent from the first independent claim, then term A must have a broader scope than term B. In other words, phrases that differ from one independent claim to another independent claim, may be interpreted to have equal scope and read on common structure yet present the structure using different terminology in order account for differing interpretation of phrase language.

The term "robotic arm" refers to a device that is typically made up of seven metal segments, joined by six joints. A computer can control the robot by rotating individual step motors which move in exact increments connected to each joint which allows the computer to move the robotic arm very precisely, repeating exactly the same movement over and over again if needed. In some embodiments, a robot or robot arms is configured to include motion sensors to facilitate accurate movement of the robotic arm.

The term "end effector" refers to the actively driven portion of the robotic arm such as the hand.

The term "autonomously" or "autonomous" refers to the ability of a robotic device and/or a robotic arm to have the ability to operate independently and not be controlled by outside forces, such as, for example humans.

The term "errant flow" refers to flow conditions that deviate from normal which are caused for example by high pressure or low pressure, air bubbles, occlusions, clots, and/or kinks in an intravenous assembly such as intravenous tubing.

The term "intravenous fluid" includes, but is not limited to 9% normal saline, Lactated Ringers, 5% Dextrose in water, 4.5% normal saline, and can include medicaments.

The term "medicament" or "medication" includes any substance (i.e., compound or composition of matter) which, when administered to an organism (human or animal) induces a desired pharmacologic and/or physiologic effect by local and/or systemic action. The term therefore encompasses substances traditionally regarded as actives, drugs or bioactive agents, as well as biopharmaceuticals typically employed to treat a number of conditions which is defined broadly to encompass diseases, disorders, infections, or the like. The medicament can be administered through intravenous administration, and can include, but is not limited to chemotherapy drugs such as doxorubicin, vincristine, cisplatin, and paclitaxel; antibiotics such as vancomycin, oxacillin, ampicillin, levofloxacin, cefazolin, meropenem, or gentamicin; antifungal drugs such as micafungin and amphotericin; pain medications such as hydromorphone and morphine; drugs for low blood pressure such as dopamine, epinephrine, norepinephrine, and dobutamine; and immunoglobulin medications (IVIG).

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

The headings below are not meant to limit the disclosure in any way; embodiments under any one heading may be used in conjunction with embodiments under any other heading.

System

Figure 2:
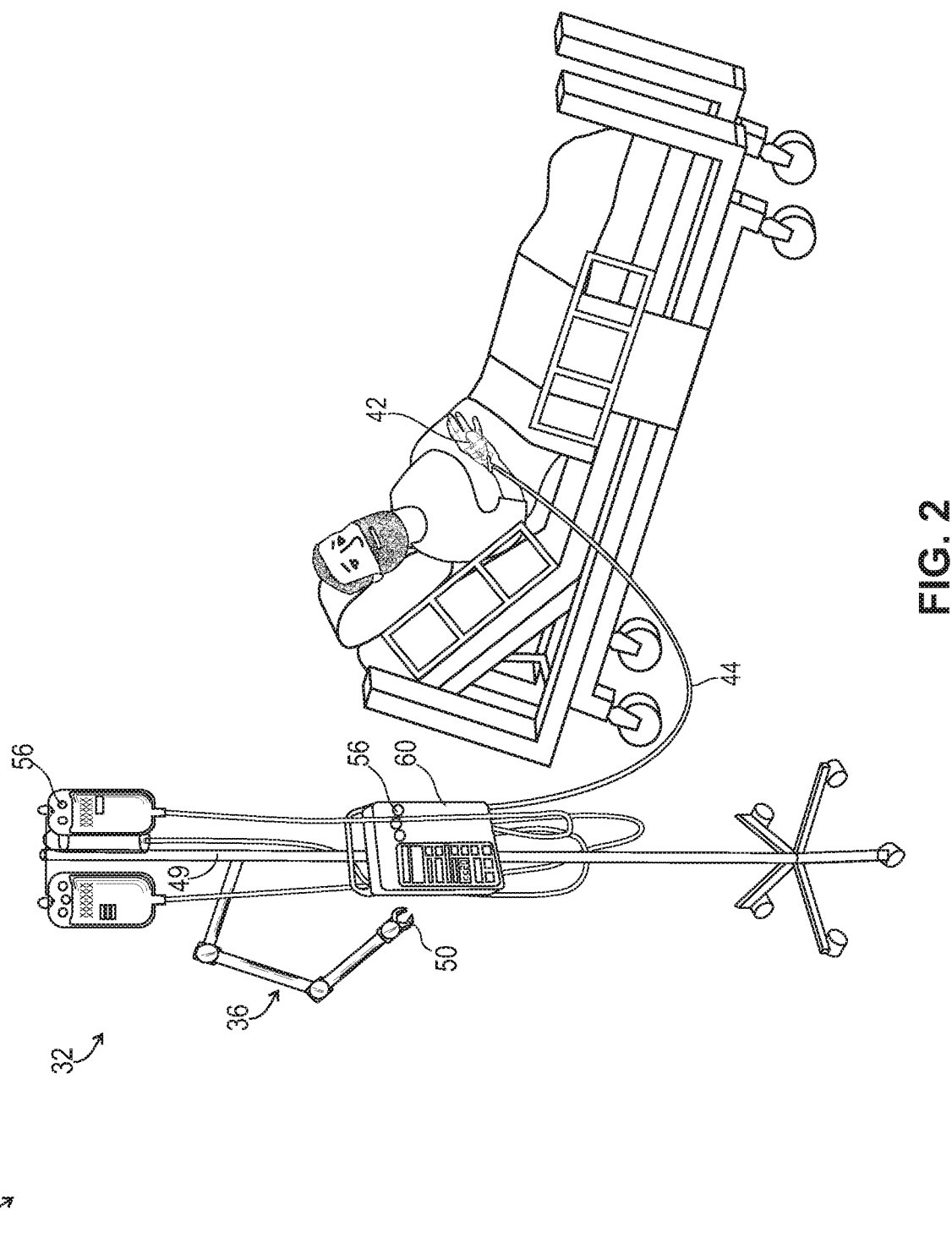
FIG. 2 is a perspective view of the system shown in FIG. 1 where the robotic device alternatively comprises a robotic arm attached to a component of the intravenous assembly.
Figure 3:
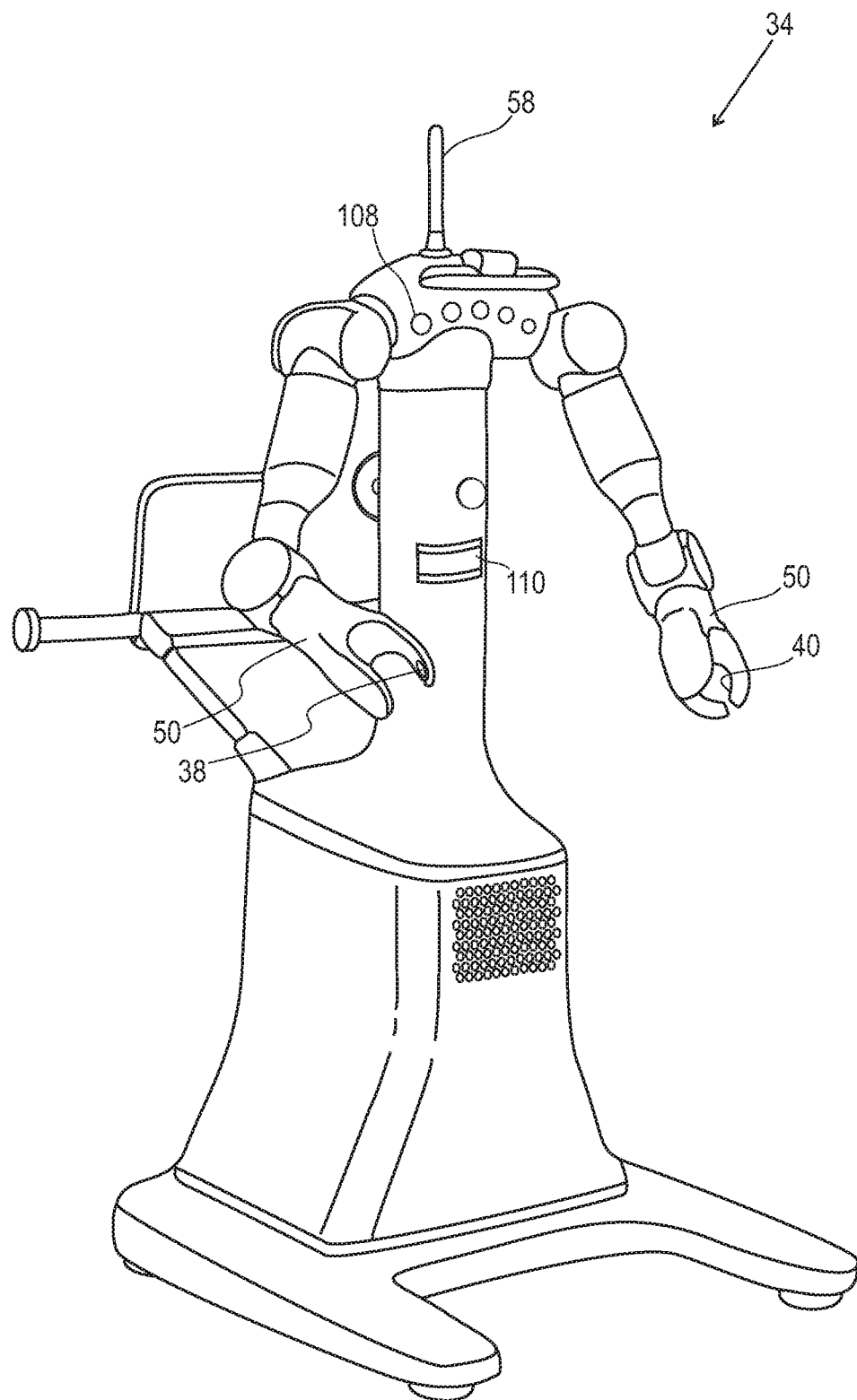
FIG. 3 is a perspective view of the robotic device of FIG. 1.
Figure 4:
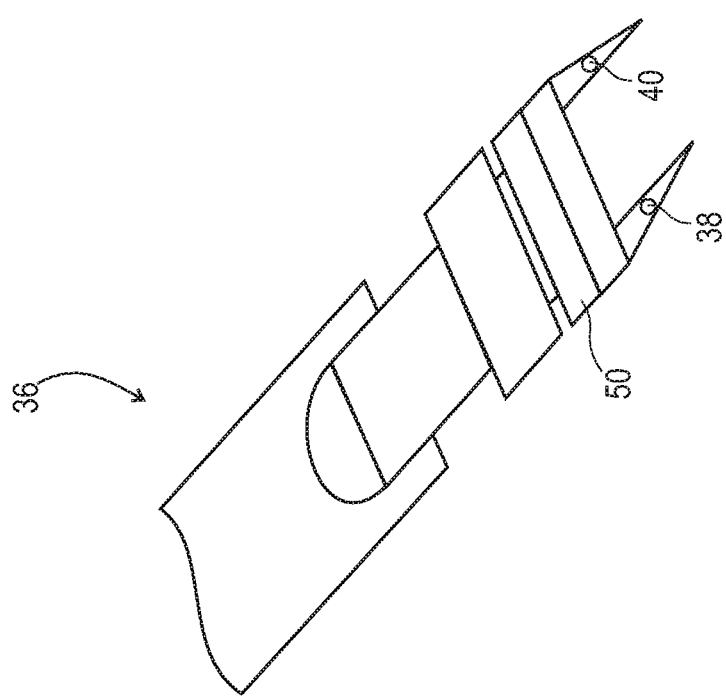
FIG. 4 illustrates a perspective view of the robotic device of FIG. 2 comprising one robotic arm.
Figure 5:
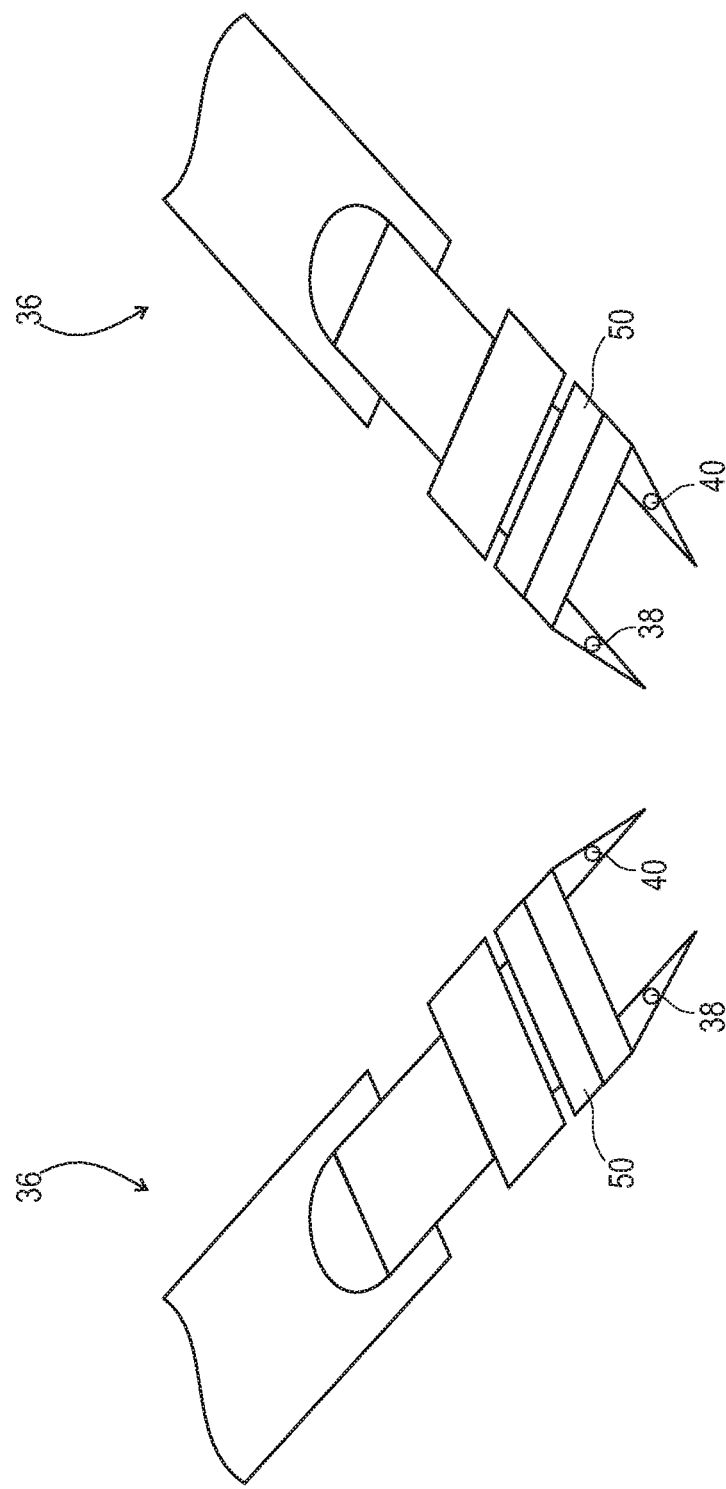
FIG. 5 is a perspective view of the robotic device of FIG. 2 alternatively comprising two arms.

A system 30 is provided, as shown in FIGS. 1-24 that monitors and maintains an intravenous assembly 32 autonomously or independently from medical staff and can prevent alarms from the intravenous assembly from being triggered. The system includes a robotic device 34. The robotic device can be a full length or humanoid robot, as shown in FIGS. 1 and 3, can be a single robotic arm 36, as shown in FIGS. 2 and 4 and/or can be two robotic arms, as shown in FIG. 5. The robotic device can be similar to the robot described in U.S. Pat. No. 10,300,597 assigned to Seiko Epson Corporation, incorporated herein by reference. The robotic device includes an optical sensor 38 that detects an errant flow in at least a component of the intravenous assembly and a pressure sensor 40 to manipulate at least the component of the intravenous assembly to restore, start, stop flow, or change at least the component of the intravenous assembly.

Figure 8:
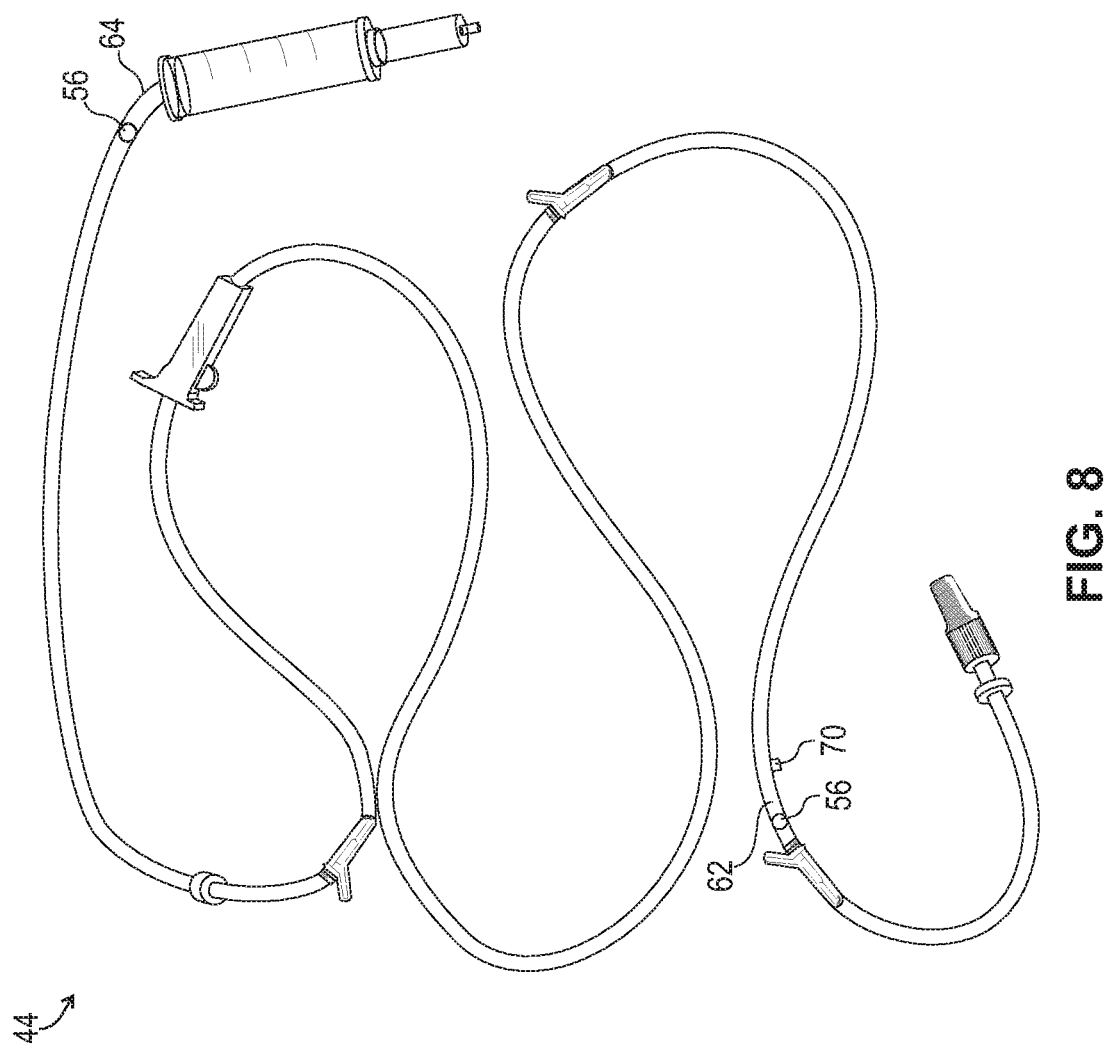
FIG. 8 is a perspective view of intravenous tubing comprising at least one sensor configured to communicate with and provide data to the robotic device. The at least one sensor is shown disposed at discrete regions such as at a proximal end and/or a distal end of the intravenous tubing.
Figure 9:
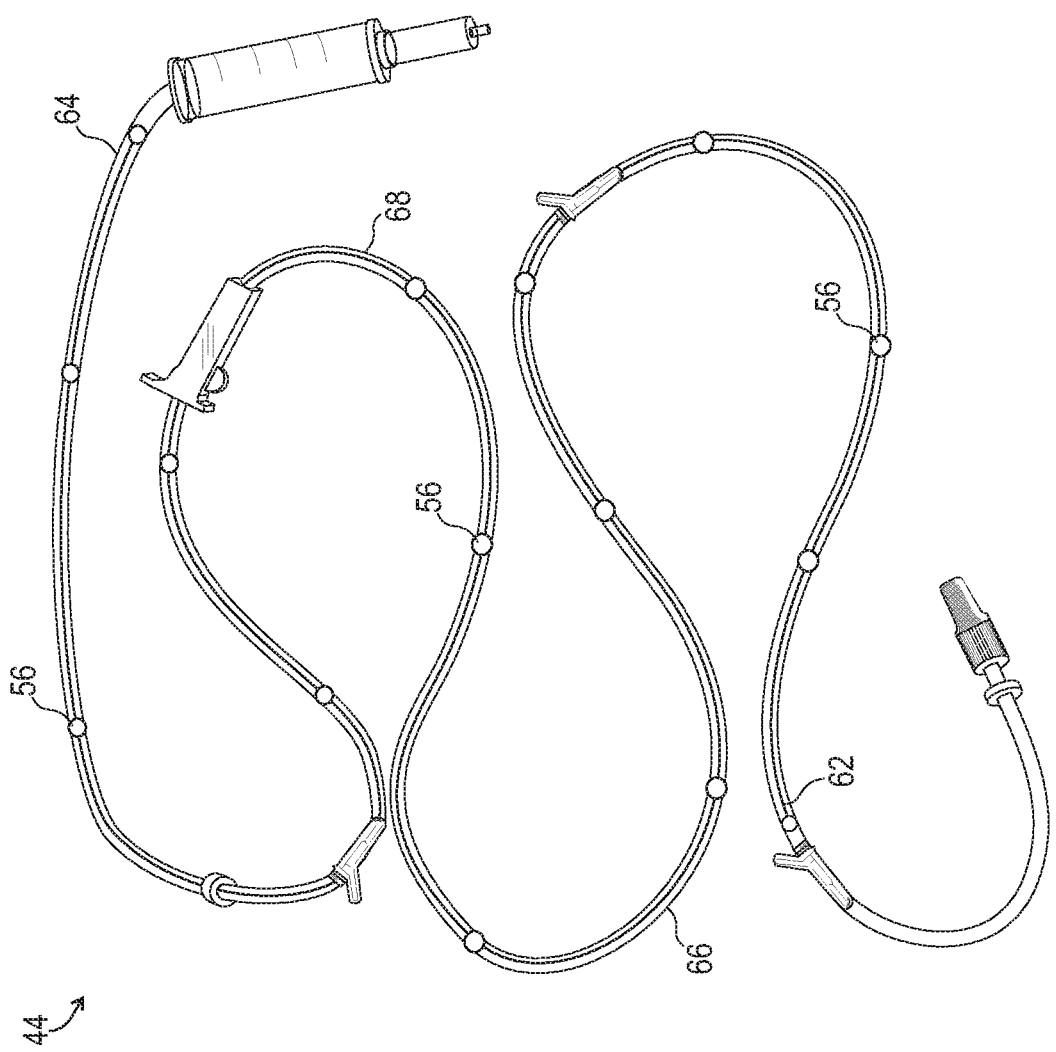
FIG. 9 is a perspective view of the intravenous tubing of FIG. 8 where the at least one sensor is a network of sensors located at continuous regions within an interior or exterior wall of the intravenous tubing.
Figure 19:
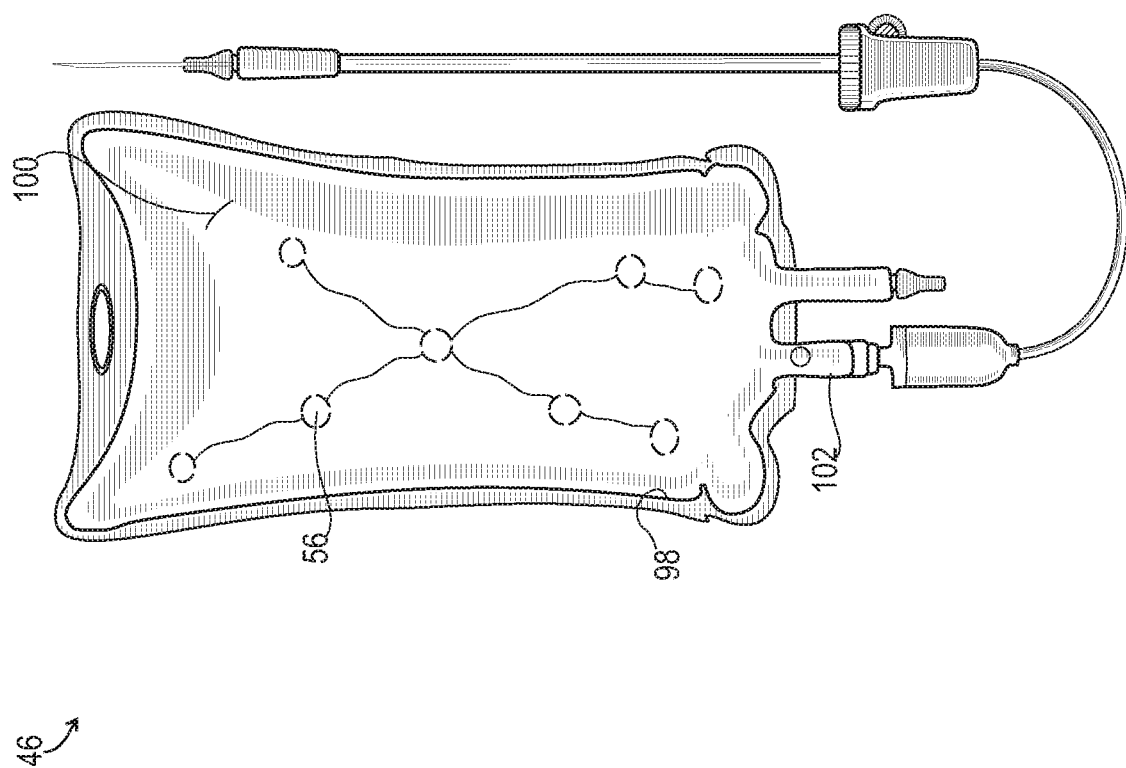
FIG. 19 is a front view of an intravenous container. The intravenous container is shown as an intravenous bag. The intravenous container comprises an interior surface and an exterior surface. The interior surface includes a network of sensors configured to communicate with and provide data to the robotic device.
Figure 20:
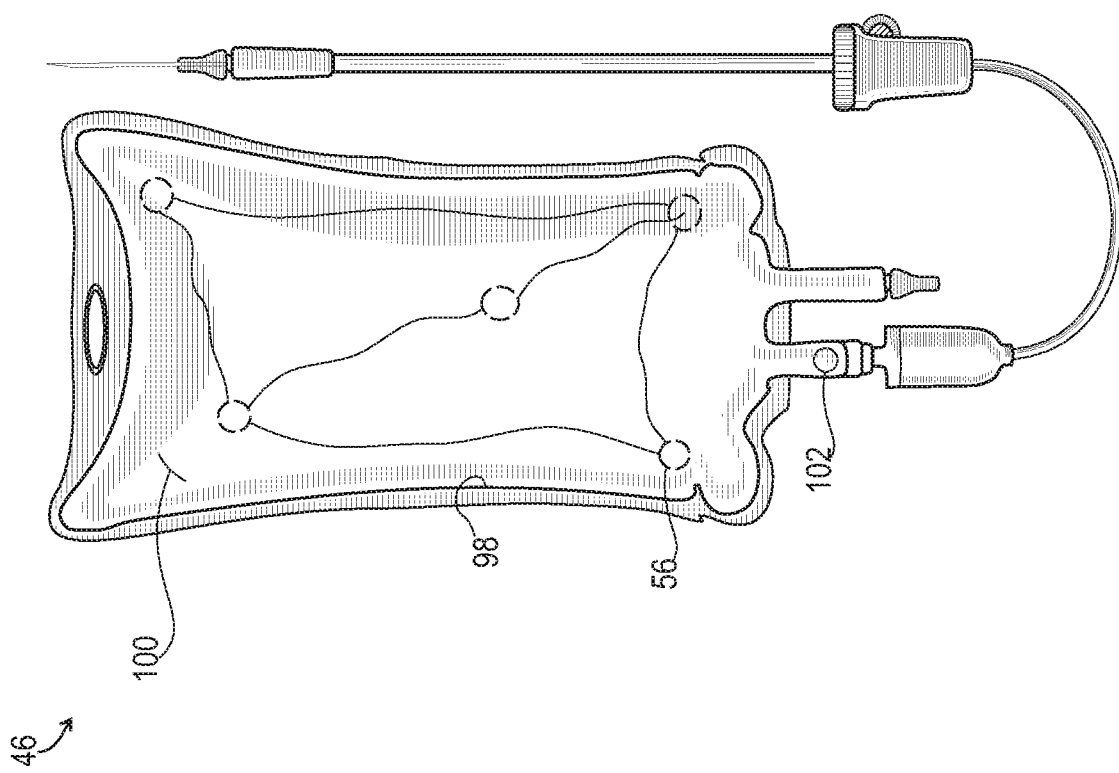
FIG. 20 is a front view of the intravenous container of FIG. 19 where the network of sensors are disposed on an exterior surface of the container.
Figure 21:
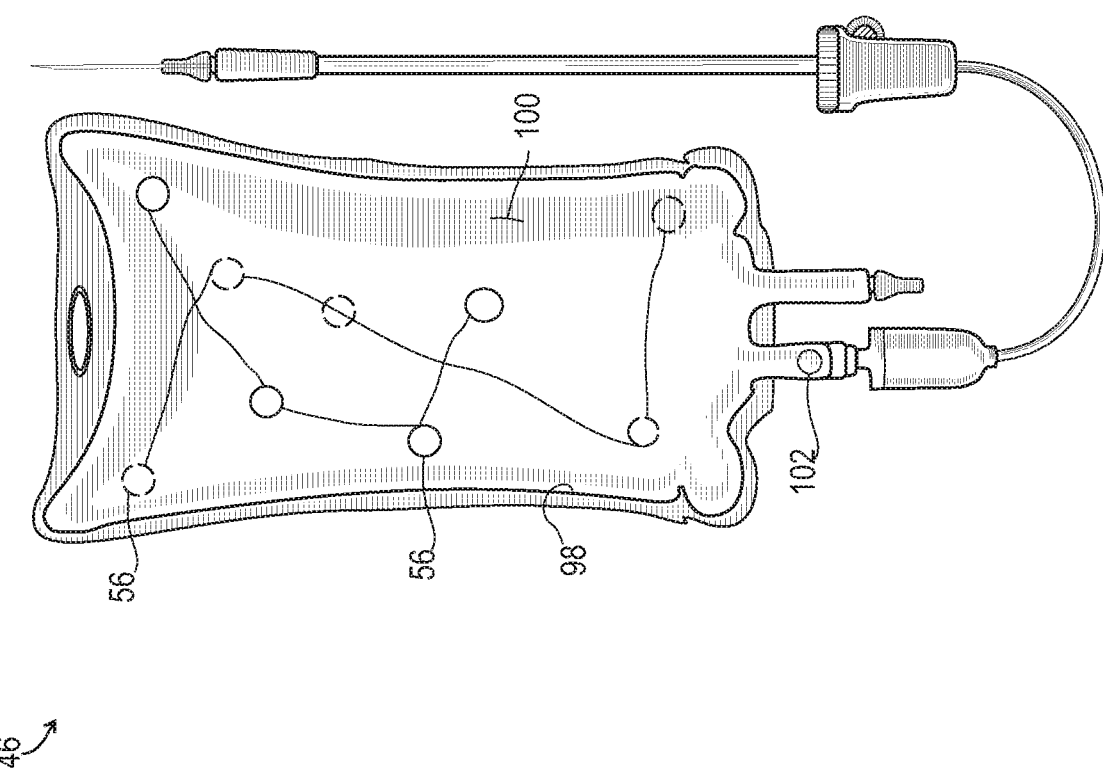
FIG. 21 is a front view of the intravenous container of FIG. 19 where the network of sensors are disposed within the interior surface and the exterior surface of the container.
Figure 23:
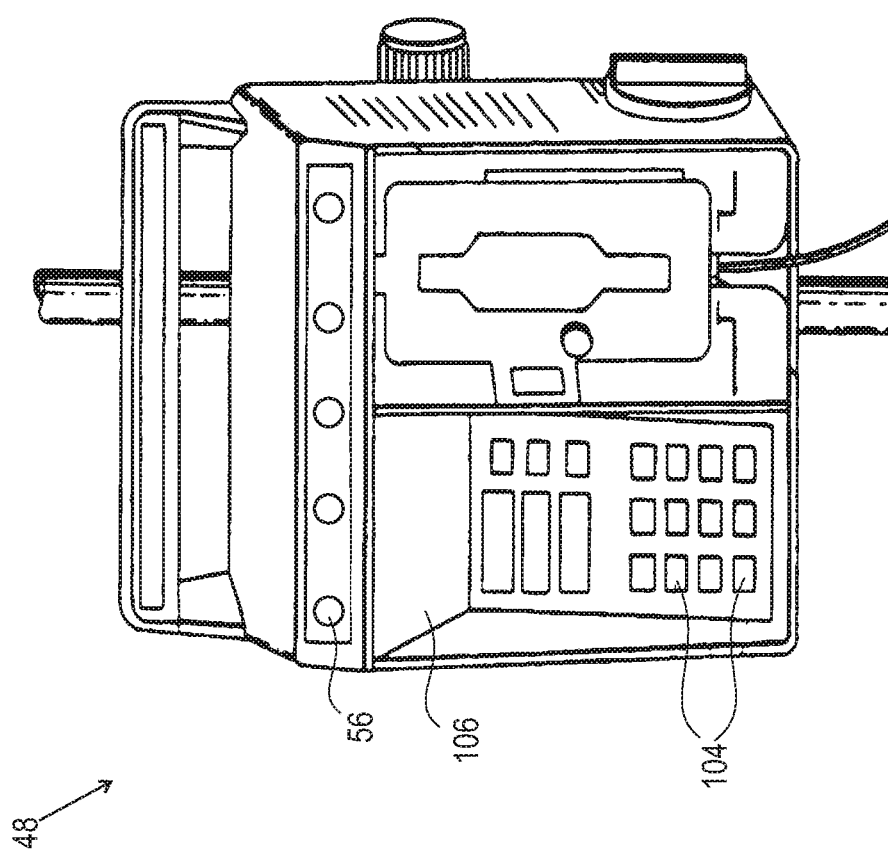
FIG. 23 is a front view of an intravenous pump comprising at least one sensor configured to communicate with the robotic device.
Figure 24:
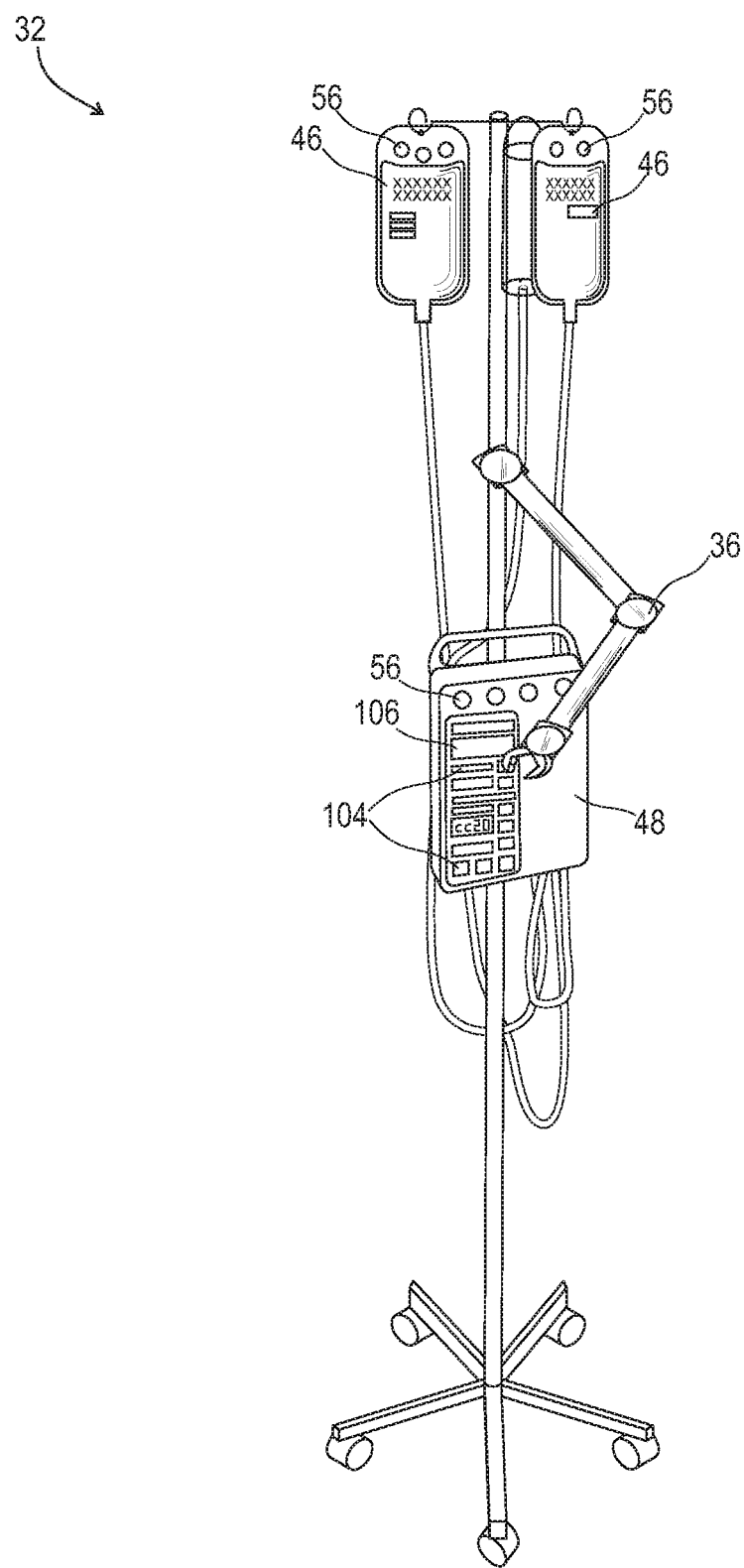
FIG. 24 is a perspective view of the intravenous assembly and the robotic arm of FIG. 4. The robotic arm is shown silencing an errant signal from being emitted by the intravenous pump of FIG. 23.

As will be described in more detail below, the intravenous assembly includes components such as an intravenous catheter 42, as shown in FIGS. 14-18, an intravenous tubing 44, as shown in FIGS. 8-9, an intravenous container 46, as shown in FIGS. 19-21 and/or an intravenous pump 48, as shown in FIGS. 23-24. The robotic arm of the robotic device is configured to engage at least one of the intravenous assembly components when an errant flow is detected by the optical sensor so that the robotic device can monitor and maintain the intravenous assembly. The robotic device can also prevent or silence an errant signal or alarm emitted by the intravenous assembly. The errant flow detected in a component of the intravenous assembly can be caused by high pressure or low pressure, air bubbles, occlusions, clots, and/or kinks in the intravenous tubing, catheter and/or the intravenous container.

Figure 6:
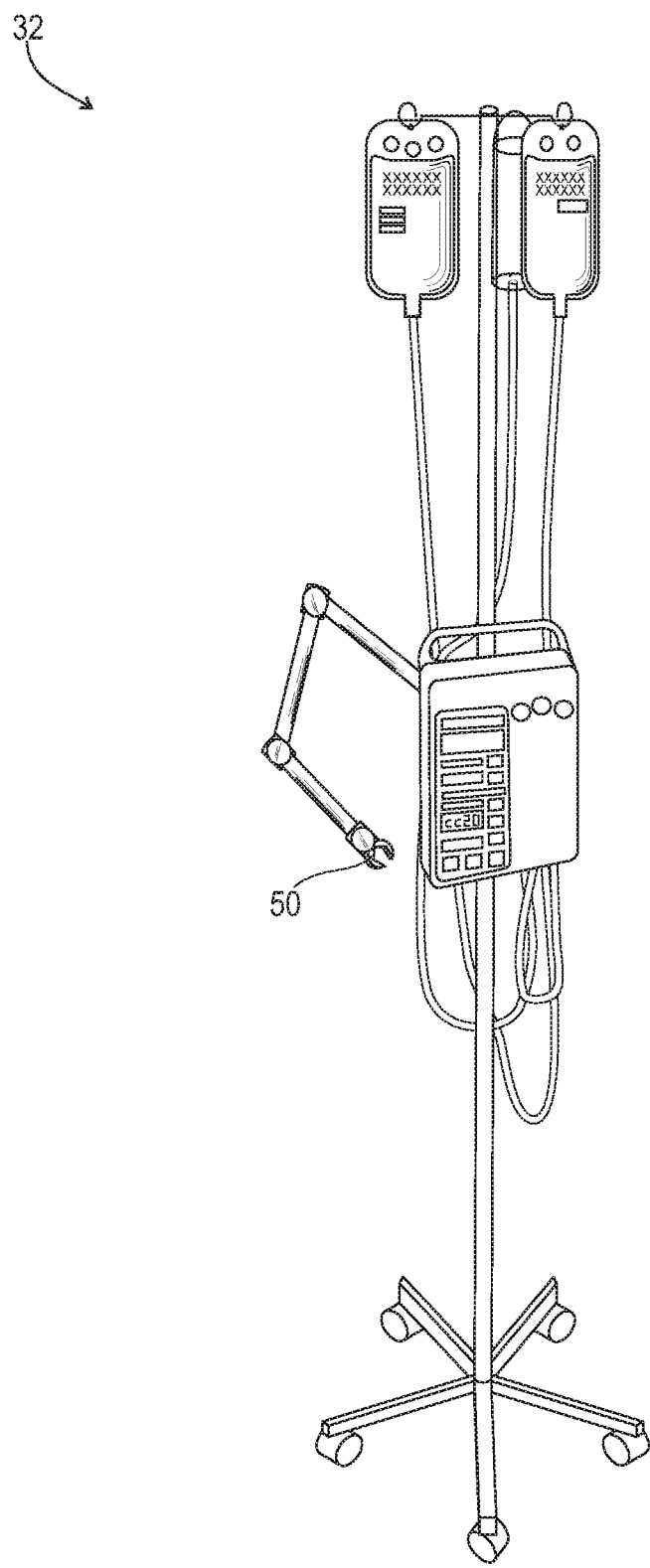
FIG. 6 is a perspective view of the robotic device of FIG. 2 comprising a robotic arm attached to a component of the intravenous assembly in the form of an intravenous pump.
Figure 7:
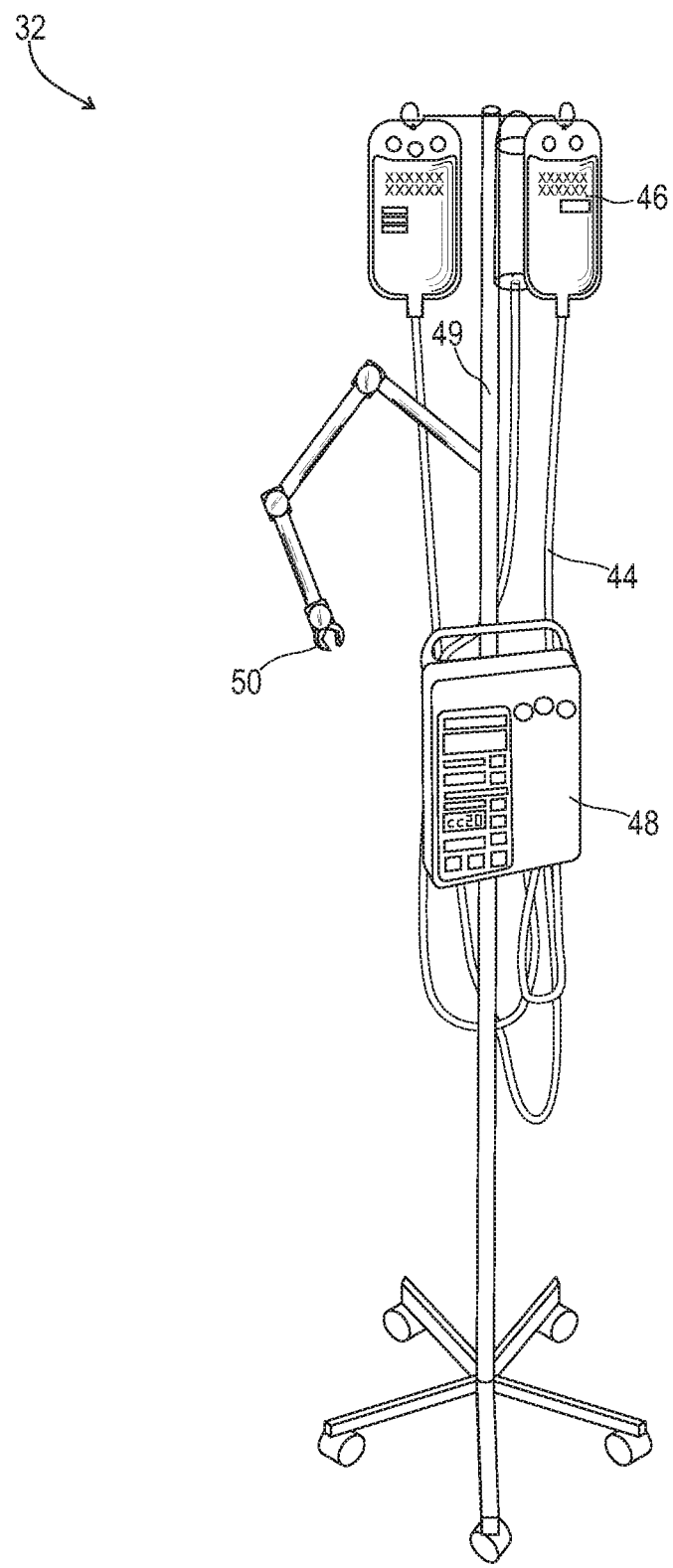
FIG. 7 is a perspective view of the robotic device of FIG. 2 comprising a robotic arm attached to an intravenous pole that holds components of the intravenous assembly.
Figure 10:
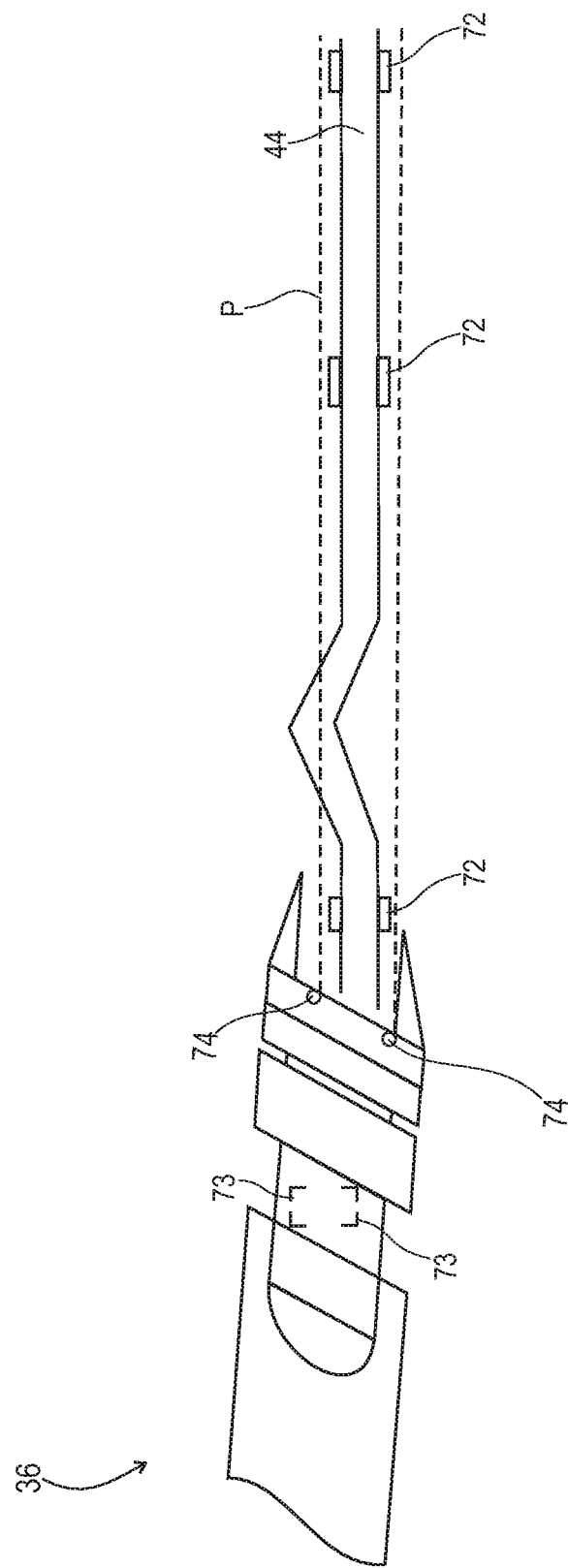
FIG. 10 is a perspective view of the robotic arm of FIG. 4 engaging the intravenous tubing to unkink the intravenous tubing. The robotic arm includes a laser sensor that forms a laser perimeter around the intravenous tubing. If a section of the intravenous tubing falls outside of the laser perimeter, the robotic arm will be alerted and the robotic arm will unkink the intravenous tubing.

The robotic arm can be made of for example, seven metal segments, joined by six joints. A processor, as described below, can control the robotic arm by rotating individual step motors (not shown) which move in exact increments connected to each joint which allows the processor to move the robotic arm very precisely, repeating the same movement if needed. A power supply can be coupled to the arm so that the arm can operate without being plugged into an electrical socket. The arm can be attached to a component of the intravenous assembly such as on the intravenous pump and/or the intravenous tubing, as shown in FIGS. 6 and 10 or attached to an intravenous pole or stand 49, as shown in FIGS. 2 and 7. It is contemplated that the robotic arm can also be added to existing intravenous assemblies.

The robotic arm can include an end effector, such as a robotic hand 50. The robotic hand can assist the robotic device in monitoring and maintaining the components of the intravenous assembly. For example, the robotic hand can be used to manipulate components of the intravenous assembly to correct issues found in the intravenous assembly by the robotic device. The robotic hand can include the pressure sensor. It is contemplated that the robotic arm and/or the hand can alternatively be manually operated by a user, such as medical staff. It is also contemplated that the end effector can include alternatives to a robotic hand such as a probe, a hook or even medical tools such as a syringe. It is to be understood that additional motors separate from the motors in the robotic arm described above are used to articulate or actuate the hand.

As described above, the robotic device includes a processor 52 that receives and processes input from the optical and pressure sensors and a controller 54 that is operatively connected to the processor and configured to operate the robotic device to manipulate at least one of the intravenous assembly components at least in part, on input from the optical and pressure sensors and processed by the processor to restore, start, stop flow, or change at least the component of the intravenous assembly.

Each of the intravenous assembly components can include at least one sensor 56 to communicate with and provide data to the robotic device. The at least one sensor can include, but is not limited to an optical sensor, a pressure sensor, a piezoelectrical sensor, an oxygen sensor, a carbon dioxide sensor, a nitrous oxide sensor, an upstream or downstream occlusion sensor, an ultrasound sensor, a sonar sensor and/or a laser sensor. The robotic device can further include a motion sensor, a piezoelectrical sensor, an ultrasound sensor, a sonar sensor and/or a laser sensor.

The optical and pressure sensors of the robotic device and the at least one sensor of a component of the intravenous assembly are capable of transmitting and receiving data through a wireless connection, such as a Bluetooth® radio wireless connection. For example, the robotic device can include a Bluetooth® radio 58 that is configured to pair with a Bluetooth® radio 60 of a component of the intravenous assembly, as shown in FIG. 1. Further, activities performed by the robotic device, alarms and maintenance of the intravenous assembly can be wirelessly and/or silently communicated to a medical station or medical staff.

As described above, the intravenous assembly includes intravenous tubing 44, as shown in FIGS. 8-9. The intravenous tubing extends from a proximal end 62 to a distal end 64 and includes the at least one sensor 56 that is configured to communicate with and provide data to the robotic device. The at least one sensor can include, but is not limited to a pressure sensor, a piezoelectric sensor, an oxygen sensor, a carbon dioxide sensor, a nitrous oxide sensor and/or an upstream or downstream occlusion sensor. The at least one sensor can be disposed at discrete positions on and/or within the intravenous tubing. For example, certain positions on the tubing are considered problem areas such as locations that are highly manipulated by medical practitioners which include the proximal and distal ends of the tubing. The sensors can also be located at an end that is closest to the patient. As shown in FIG. 8, disposing a sensor at the proximal end and/or the distal end of the intravenous tubing will increase the likelihood that a sensor will accurately detect a cause of errant flow. Suitable intravenous tubing that can be used for example in the intravenous assembly as described above include intravenous tubing that is manufactured by Baxter (owned by Baxter Healthcare Corporation, an Illinois corporation).

The at least one sensor can also be a network of sensors that are located in continuous regions within an interior 66 and/or exterior wall 68 of the intravenous tubing. For example, as shown in FIG. 9, the network of sensors can be located along an entire length of the interior and/or exterior wall of the intravenous tubing. The sensors can be embedded within the interior and/or exterior wall and/or can be monolithically formed with the interior and exterior walls. The network of sensors can include more than 1 to about 100 sensors. For example, a network of sensors can include 2, 3, 4, 5, 6, 7, 8, 9, 10, 15, 20, 25, 30, 35, 40, 45, 50, 55, 60, 65, 70, 75, 80, 85, 90, 95 to about 100 sensors.

The intravenous tubing may also include at least one valve, such as an outlet valve 70 configured to facilitate release of air trapped within the interior of the intravenous tubing, as shown in FIG. 8. When the at least one sensor detects air or gas bubbles within the intravenous tubing, the at least one sensor can communicate through the wireless connection or other electronic means to the robotic device so that the valve can be opened to release the air or gas bubbles or to flush out the bubbles from the tubing.

The valve can be opened and a syringe (not shown) or a laser (not shown) can be inserted into the valve by the robotic device so that air can be evacuated by the syringe or laser. The valve can also be used to laser or flush the intravenous tubing with saline to eliminate clots in the tubing. The valve can be opened by the robotic device, medical staff, and/or automatically. The valve can include a duckbill valve and/or a flap valve. The valve can be disposed at an end of the tubing or multiple valves can be disposed along the length of the tubing.

The intravenous tubing may be made from a memory foam material. The memory foam material can be manufactured from visco-elastic memory foam, but other foam materials may be used including foams made from silicon, various plastics, polyvinylchloride (PVC) and polyethylene. The memory foam material can have a varying elasticity depending on the desired flexibility or stiffness of the tubing. Because of the properties of the memory foam material, the tubing will be able to unkink or untwist itself automatically.

The intravenous tubing can be macro intravenous tubing (10, 15, or 20 gtts/min) and/or micro intravenous tubing (60 gtts/min). The intravenous tubing can include peripheral lines, central lines, midline catheter lines, continuous infusion lines, secondary IV, IV push, and/or volume expanders.

As shown in FIG. 10, the robotic hand is configured to engage the intravenous tubing to unkink or untwist the intravenous tubing. The intravenous tubing can include attachment points 72 or a track disposed on the exterior wall of the tubing that facilitates movement of the robotic hand having corresponding attachments 73 that engage with the attachment points along the entire length of the tubing to unkink the tubing. The robotic arm or hand can include one or more laser sensors 74 that form a laser perimeter P around the intravenous tubing. If a section of the intravenous tubing falls outside of the laser perimeter, then the robotic arm will be alerted and the robotic arm will unkink or untwist the intravenous tubing.

Figure 11:
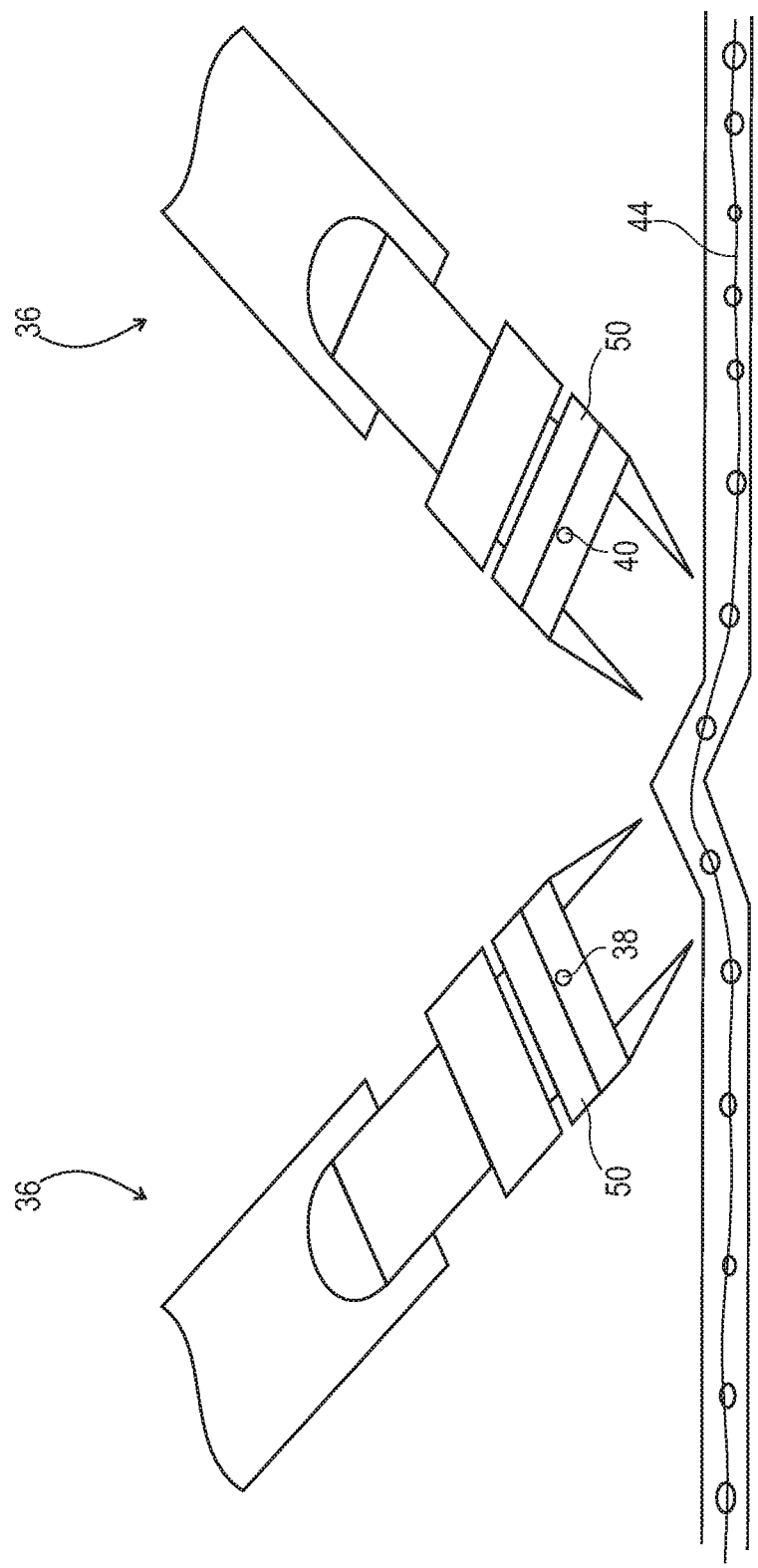
FIG. 11 is a perspective view of the robotic arms of FIG. 5 engaging the intravenous tubing to unkink the intravenous tubing.

Alternatively, when two robotic arms or hands are employed, as shown in FIGS. 3 and 11, the optical sensor and the pressure sensor of the robotic device can detect a kink or twist in the intravenous tubing and the two robotic arms with hands will unkink or untwist the tubing. The robotic device can also preemptively correct the intravenous tubing prior to when a kink or twist in the tubing fully develops when the at least one sensor detects that the flow rate within the tubing has decreased.

Figure 12:
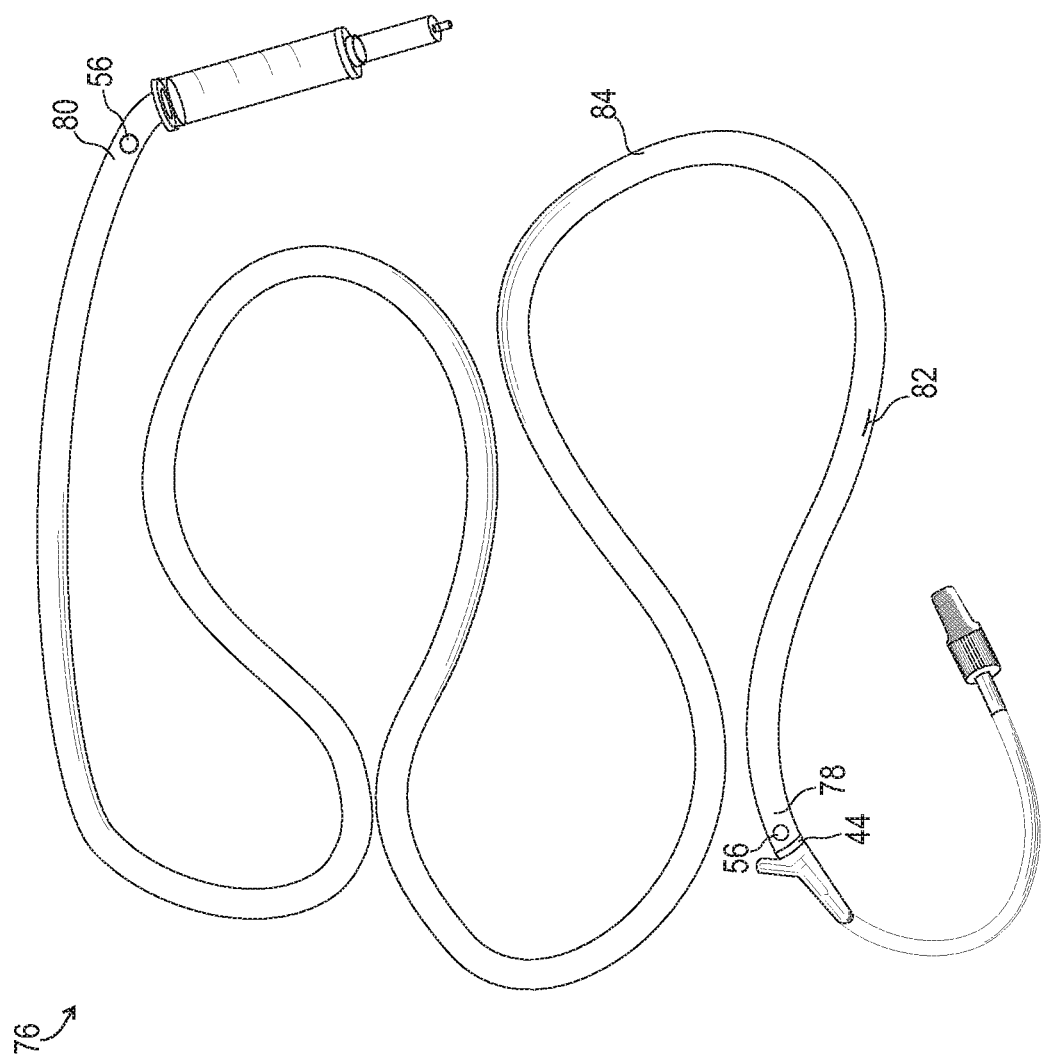
FIG. 12 is a perspective view of the intravenous tubing of FIG. 8 disposed within a sleeve. The sleeve includes sensors disposed at discrete regions such as at a proximal end and/or a distal end of the sleeve. The sensors are configured to communicate with and provide data to the robotic device.
Figure 13:
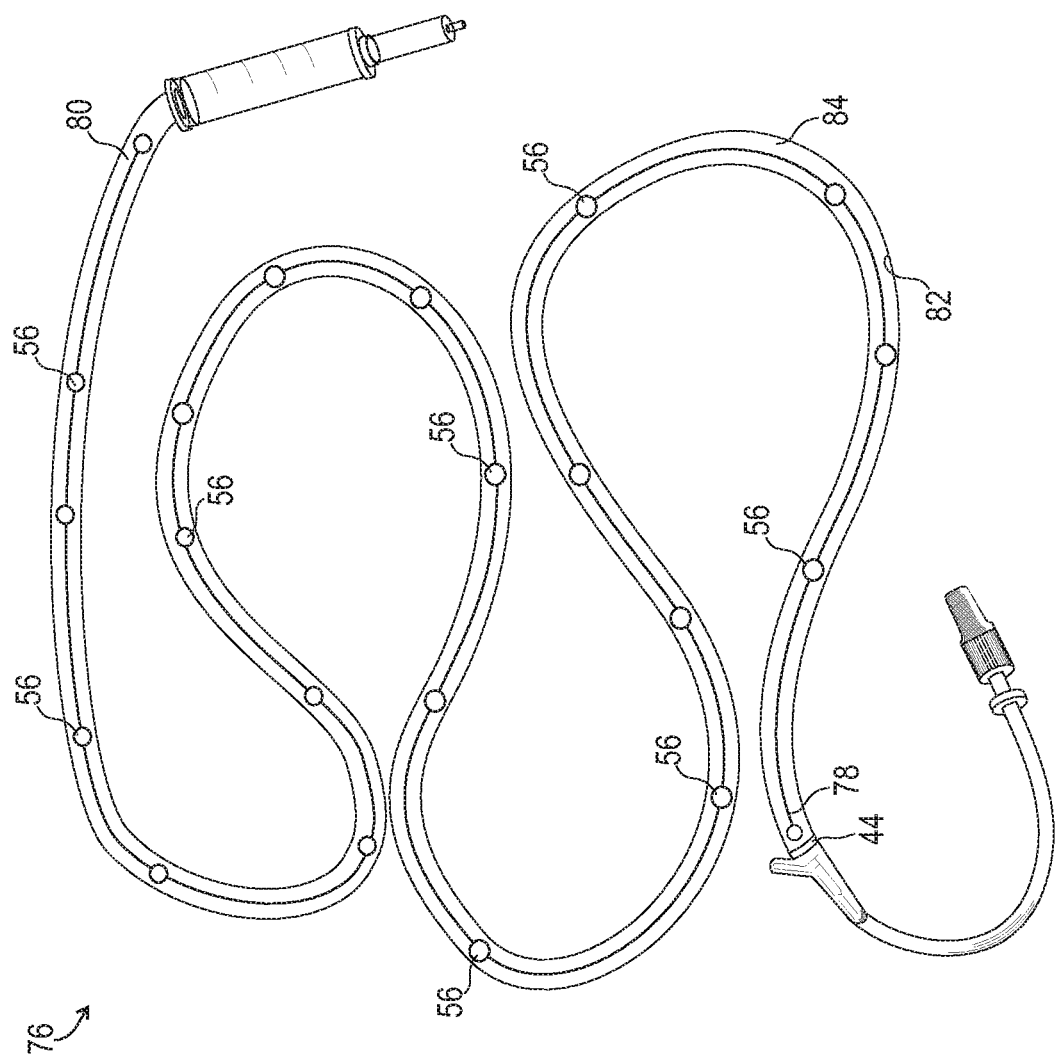
FIG. 13 is a perspective view of the sleeve of FIG. 12 shown with a network of sensors disposed at continuous regions along an entire length of the sleeve.

As shown in FIGS. 12-13, the intravenous tubing can be disposed within a sleeve 76. The sleeve includes a proximal end 78 and a distal end 80 and includes at least one sensor 56 configured to communicate with and provide data to the robotic device. As shown in FIG. 12, the at least one sensor can be disposed on the proximal end and/or the distal end of the sleeve on an exterior surface 82 and/or on an interior surface 84. As shown in FIG. 13, the sleeve can include a network of sensors disposed along an entire length of the sleeve. The sleeve can be employed with the intravenous tubing when the tubing does not include sensors or even if the tubing does include sensors. The sleeve can also be reusable.

The sleeve can have a thickness from about 1 millimeter (mm) to about 10 mm, from about 1 mm to about 8 mm, from about 1 mm to about 6 mm, or from about 1 mm to about 4 mm. The thickness of the sleeve can also vary depending on the location. For example, the thickness of the sleeve can be greater in areas along the length of the sleeve that do not contain sensors and less thick in areas that contain a sensor.

The intravenous assembly includes catheter 42, as shown in FIGS. 14-18. The catheter extends from a first end 86 to a second end 88. At the first end, a needle 90 is provided that is configured for disposal within an entrance of a patient's blood vessel and is configured for insertion into the blood vessel of the patient. The catheter includes at least one sensor 56 disposed within an interior 92 and/or exterior 94 of the catheter, and is configured to communicate with and provide data to the robotic device.

Figure 14:
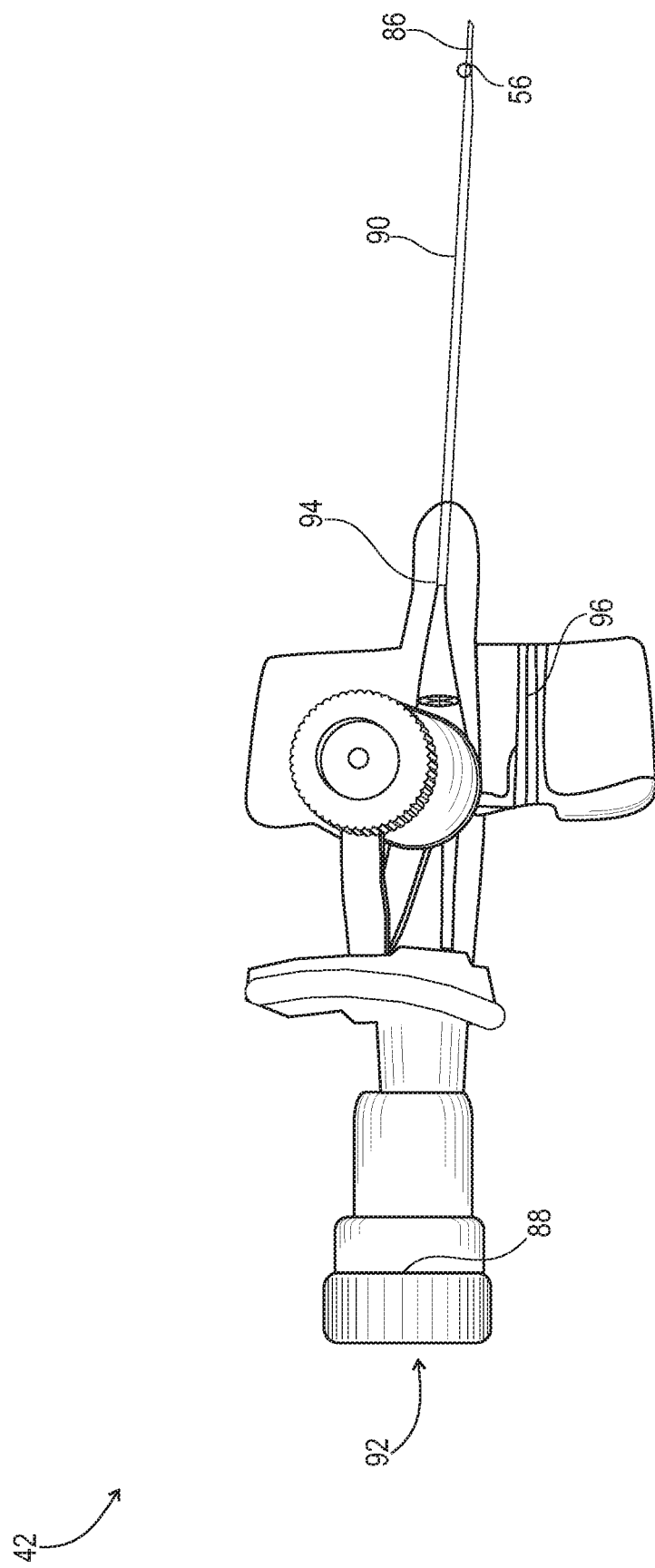
FIG. 14 is perspective view of a catheter comprising a sensor disposed at an end of a catheter needle. The end of the catheter needle is configured for disposal within an entrance of a patient's blood vessel. The sensor is configured to communicate with and provide data to the robotic device.
Figure 15:
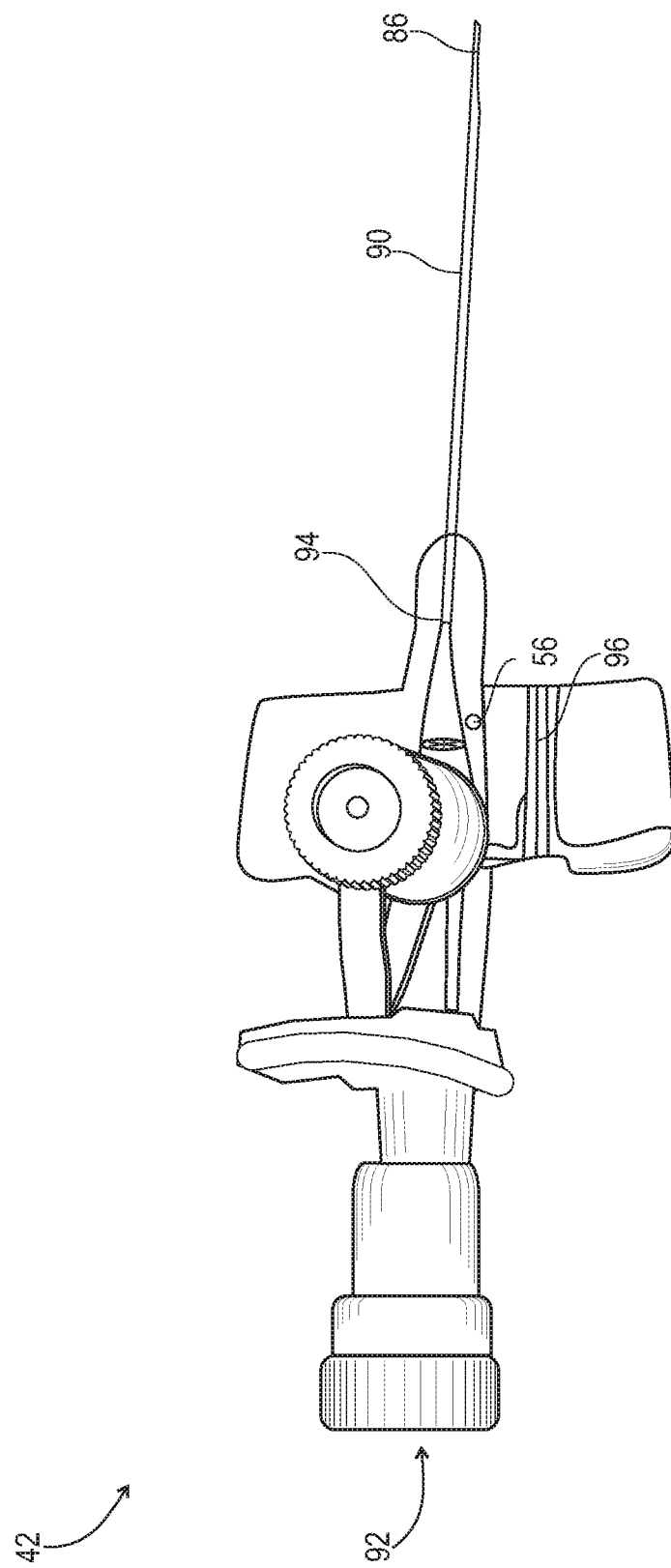
FIG. 15 is a perspective view of the catheter of FIG. 14 where the sensor is disposed within a hub of the catheter.

As shown in FIG. 14, the at least one sensor can be disposed at an end of the needle. The at least one sensor can also be disposed within or on a hub 96 of the catheter, as shown in FIG. 15. The at least one sensor can be a network of sensors, and a sensor can be located on the end of the needle as well as within the hub of the catheter. The network of sensors can also be disposed throughout the entire length of the catheter. The at least one sensor can include a pressure sensor, a piezoelectric sensor, an oxygen sensor, a carbon dioxide sensor, a nitrous oxide sensor and/or an upstream or downstream occlusion sensor.

Figure 16:
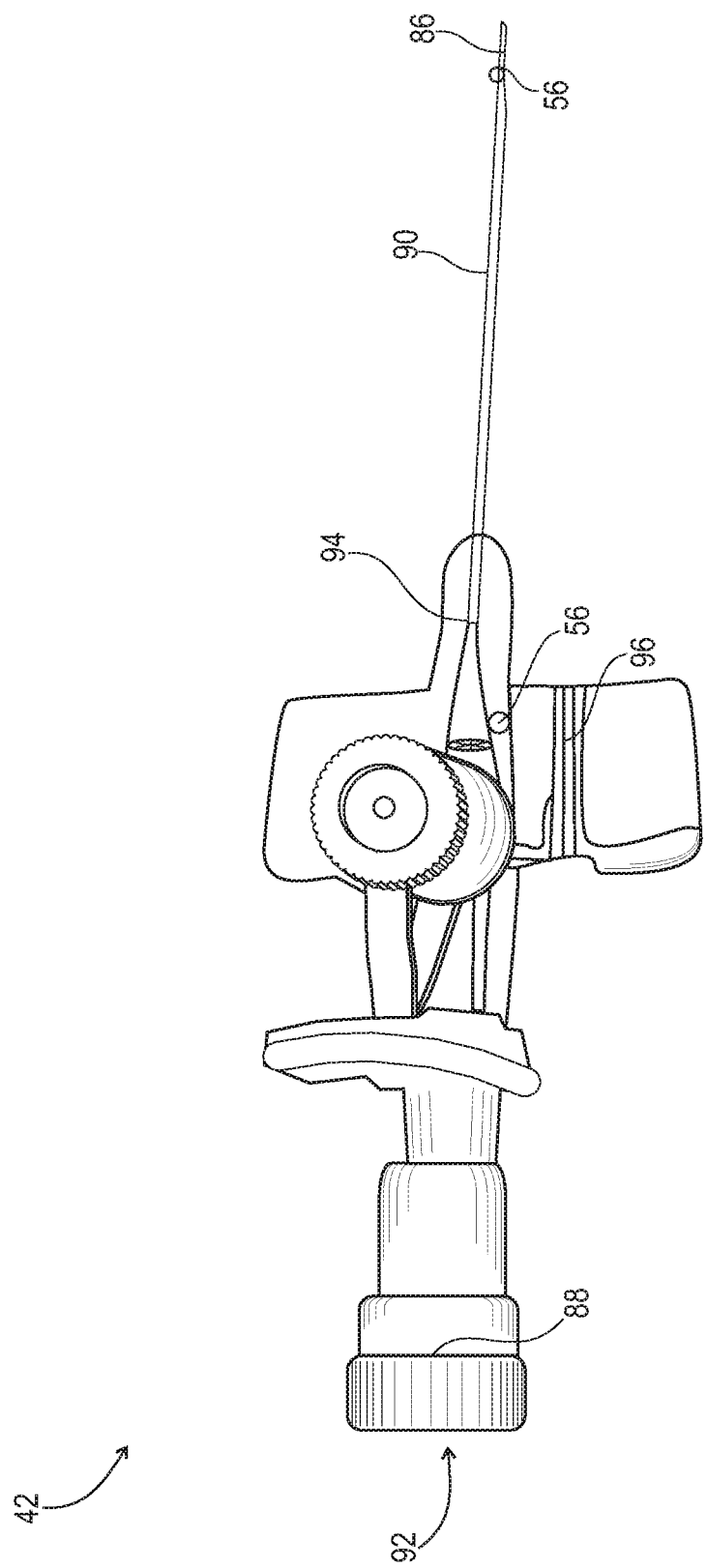
FIG. 16 is a perspective view of the catheter of FIG. 14 where the catheter includes a sensor disposed at an end of a catheter needle and a sensor disposed within a hub of the catheter.
Figure 17:
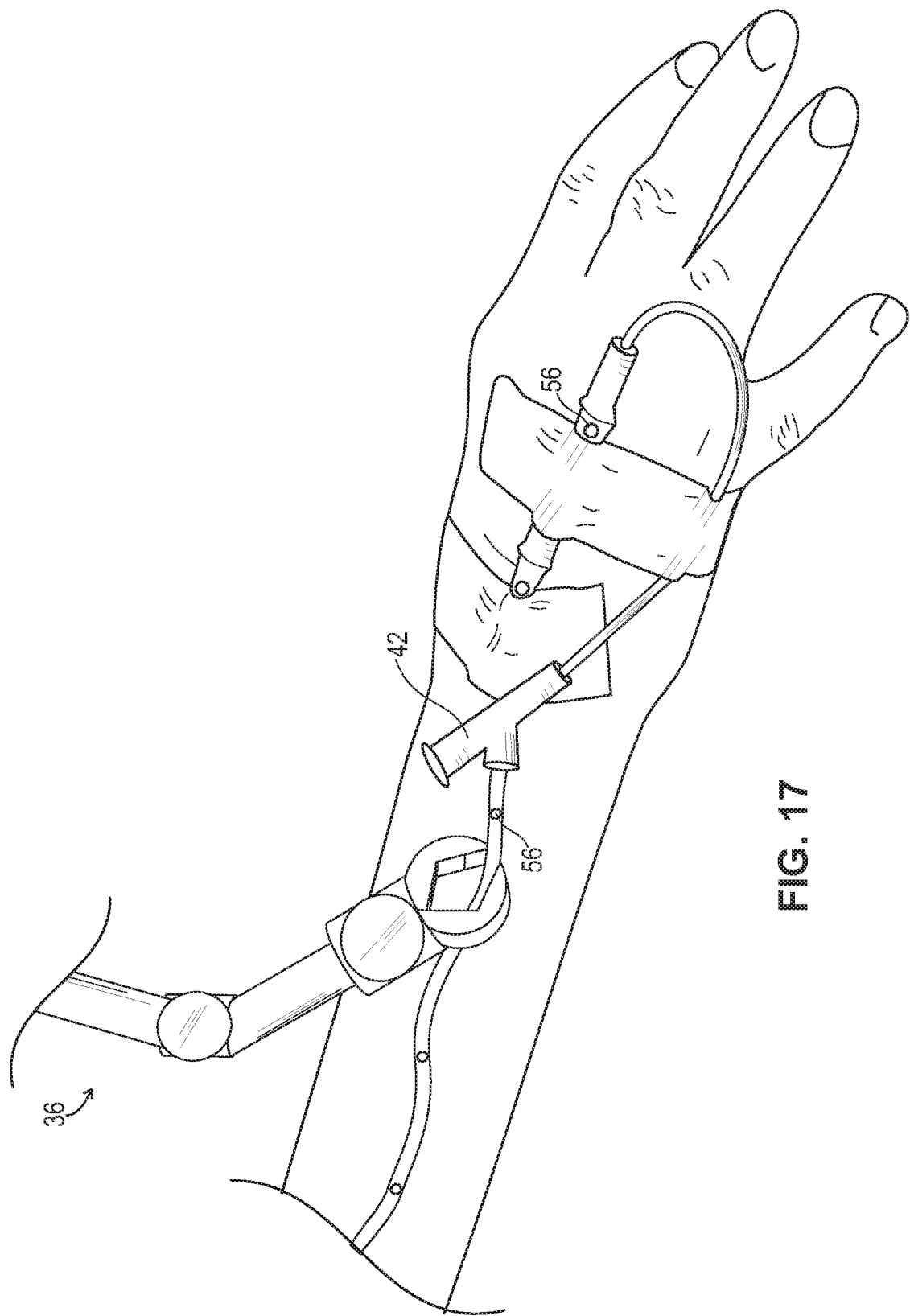
FIG. 17 is a perspective view of the catheter of FIG. 14 and the robotic arm of FIG. 4. The robotic arm is shown engaging the catheter to remove the old catheter so that a new catheter can be inserted into a patient.
Figure 18:
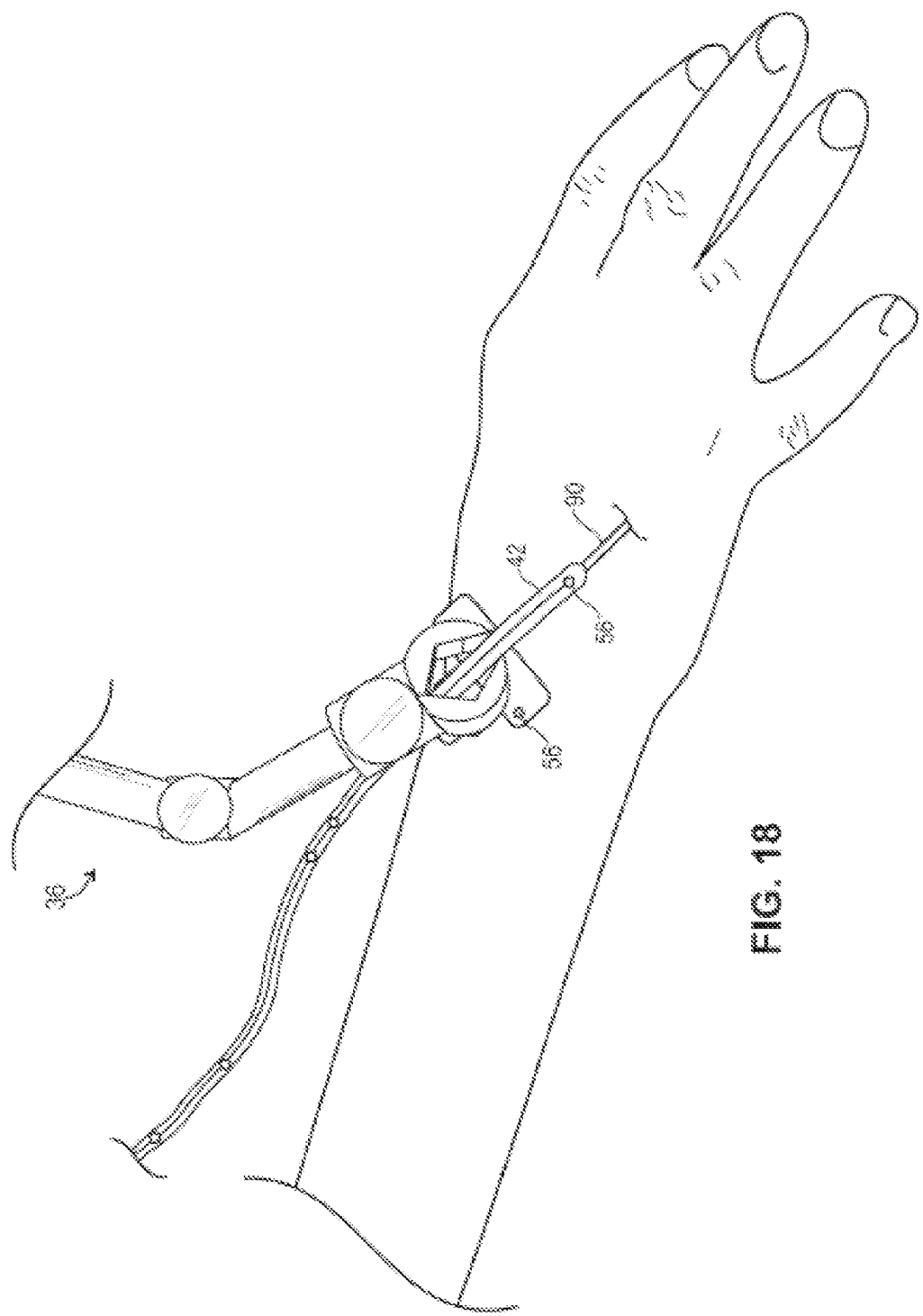
FIG. 18 is a perspective view of the catheter of FIG. 14 and the robotic arm of FIG. 4. The robotic arm is shown engaging a new catheter so that the new catheter can be inserted into a patient.

As shown in FIGS. 16 and 17, the robotic hand is configured to engage an old catheter (FIG. 17) to remove and/or insert a new catheter (FIG. 18) into a patient. To assist in inserting a new catheter, the robotic device can include and/or can be coupled with ultrasound guidance or a Doppler attachment. By implementing the robotic device to insert a new catheter into the patient, the amount of air bubbles in the catheter and the intravenous tubing will decrease or be prevented from forming.

FIGS. 19-22 illustrate the intravenous container 46 of the intravenous assembly. The intravenous container can be a clear plastic bag or a glass container and includes an interior surface 98 and an exterior surface 100. The interior surface and/or the exterior surface can include at least one sensor 56 configured to communicate with and provide data to the robotic device. The at least one sensor can include a pressure sensor, an oxygen sensor, a carbon dioxide sensor, a nitrous oxide sensor, an ultrasonic sensor, a piezoelectric sensor, an electromagnetic sensor, an inductive or capacitive sensor, and/or an upstream or downstream occlusion sensor.

As shown in FIG. 19, the at least one sensor can include a network of sensors disposed continuously throughout the interior surface of the intravenous container. Alternatively, a network of sensors can be disposed on the exterior surface of the intravenous container, as shown in FIG. 20, or a network of sensors can be disposed on both the interior surface and exterior surface of the intravenous container, as shown in FIG. 21. Additionally, a sensor can be located within a port 102 of the intravenous container, as shown in FIG. 19.

Figure 22:
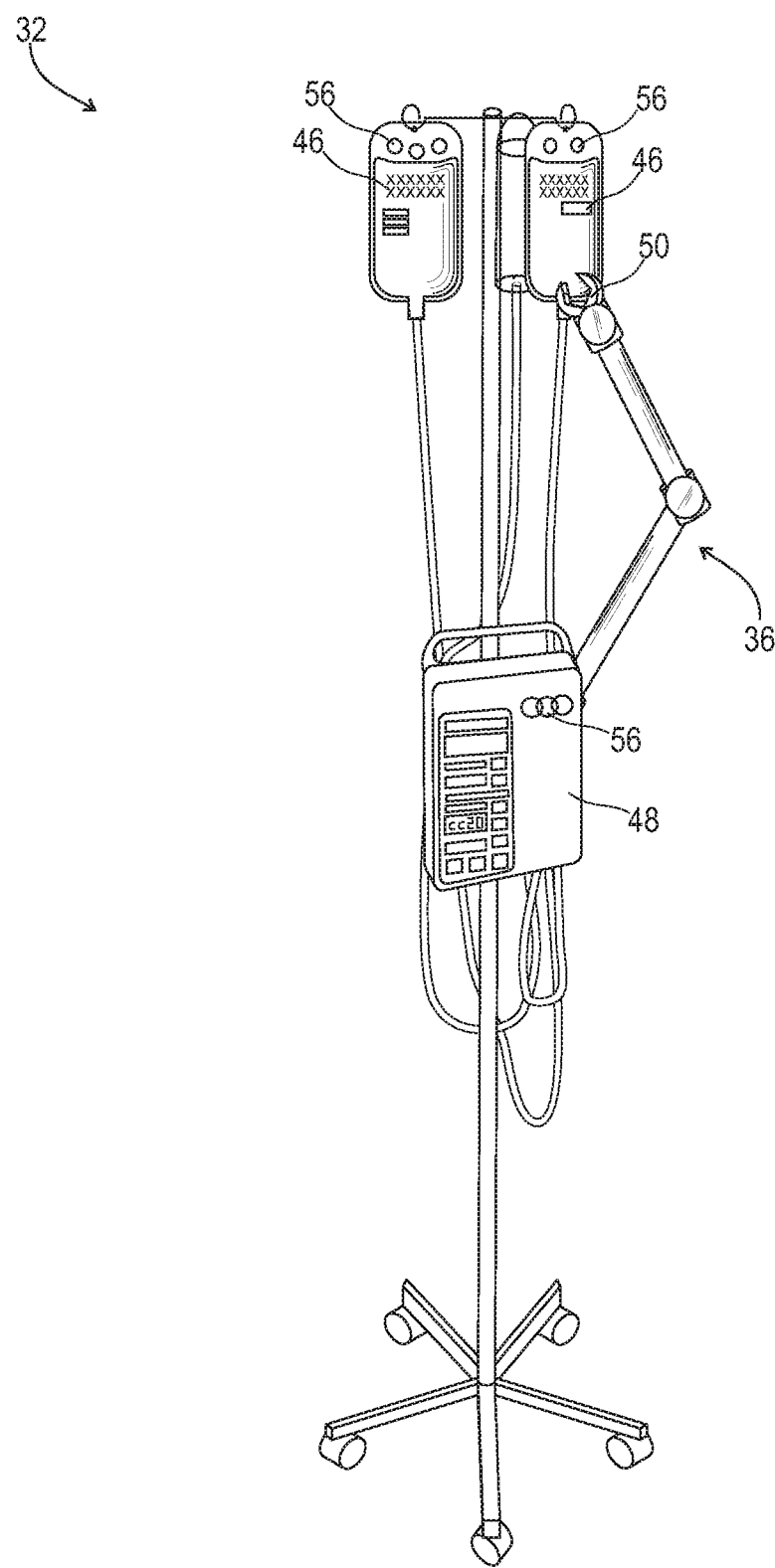
FIG. 22 is a perspective view of the robotic device of FIG. 2. The at least one sensor of the intravenous container is communicating with the robotic device so that the robotic arm replaces the intravenous container when it is empty.

The at least one sensor of the intravenous container is configured to communicate with at least one sensor of a second intravenous container and the robotic device to replace the intravenous container with the second intravenous container when the intravenous bag is empty or nearly empty, as shown in FIG. 22. The second intravenous container can be alerted to start infusing fluid once the original intravenous container is empty or nearly empty so that a continuous and seamless infusion can occur. Valves or tubing attached to each of the containers can also contain sensors and be in communication with each other so that the valve in the original container closes as the other valve of the second container opens for infusion. The at least one sensor is also capable of communicating with the robotic device alone to replace the intravenous container when it is empty. The intravenous containers and the robotic device can communicate through the Bluetooth® wireless connection described above or through other electronic means. By implementing the robotic device to replace the old intravenous bag with a new one, the amount of air bubbles that would form from replacement of the intravenous bag manually will decrease or be prevented.

The intravenous container can include a flow sensor and/or a volume sensor. The flow and/or volume sensor can provide data on the amount of fluid remaining in the intravenous container so that the robotic device knows when to remove and/or replace the intravenous container.

In addition to sensors being used to detect errant flow in the components of the intravenous assembly, a handheld spectrophotometer can also be used by the robotic device and/or the medical staff to detect if there is precipitation and/or a clot in the intravenous tubing and/or the intravenous container. For example, handheld spectrophotometers that can be used in conjunction with this system are manufactured by TruScan™ (owned by Thermo Scientific™, a Delaware corporation).

FIG. 23 illustrates the intravenous pump 48 of the intravenous assembly. The intravenous pump includes at least one sensor configured to communicate with and provide data to the robotic device. The at least one sensor can include a pressure sensor, an oxygen sensor, a carbon dioxide sensor, a nitrous oxide sensor, an optical sensor, a piezoelectrical sensor, an upstream or downstream occlusion sensor, an ultrasound sensor, a sonar sensor and/or a laser sensor. Similar to the other components of the intravenous assembly described above, the at least one sensor of the pump can be a network of sensors.

As shown in FIG. 24, the robotic device can engage and interact with the infusion pump with the robotic arm and hand. For example, the robotic device can prevent or silence an errant signal or alarm emitted by the intravenous pump by directly interfacing with buttons 104 and/or a screen 106 of the pump.

The intravenous pump can include various types of pumps including, but not limited to a large volume pump, a patient controlled pump, an insulin pump, an elastomeric pump, an enteral pump, a syringe pump, an ambulatory pump, and a stationary infusion pump. Additionally, the infusion pump may also be may be applied to intra-arterial infusion. Suitable intravenous pumps that can be used for example in the intravenous assembly as described above include pumps that are manufactured by Baxter (owned by Baxter Healthcare Corporation, an Illinois corporation).

It is contemplated that the pump can be wirelessly charged to eliminate the need for plugging the pump into an electrical socket. Wireless charging would prevent a low battery and a low battery alarm signal from being triggered. A wireless charger can be placed in every patient room at a hospital or medical facility. The pump can alternatively be equipped with a battery that is larger than a standard sized battery that is typically included with an intravenous pump.

The at least one sensor can alternatively be detachable from components of the intravenous assembly described above. For example, the at least one sensor can be attached to the exterior surface or exterior wall of components of the intravenous assembly by adhesive, adhesive strips, Velcro®, clips, hooks, magnets, snaps, buttons, interference fittings, friction fittings, compressive fittings, posts, connectors, and/or fixation plates. It will be understood, that although the at least one sensor is shown as a circular shape, other shapes are contemplated such as, rectangular, crescent, oval, square, hexagonal, pentagonal, and/or triangular.

The robotic device can include indicia, such as LEDs 108 located on an exterior surface of the robotic device, as shown in FIG. 3. The LEDs can indicate when the robotic device is monitoring, maintaining and correcting components of the intravenous assembly. The indicia can be one or more LED lights used as visual indicators. The LEDs can be various colors, such as, for example, blue, red, yellow, white, green, purple, pink and/or orange to visually indicate to medical staff what component of the intravenous assembly is being maintained or corrected.

The robotic device can include a display 110, as shown in FIG. 3, on an exterior surface that displays indicia to indicate to medical staff or a patient what component of the intravenous assembly is being maintained or corrected. The display can include device(s) such as 412 liquid crystals display (LCD), flat panel, or a solid state display. It is contemplated that the robotic device can also include a speaker and/or a remote control.

The robotic device may also include an imaging unit such as an image sensor or camera including CMOS (complementary metal-oxide semiconductor) and CCD (charge-coupled device) which can aid in determining coordinates associated with a patient's blood vessel when disposing a catheter into a patient with the robotic device. It is contemplated that a laser rangefinder which uses a laser beam to determine the distance to an object can also be used in connection with the robotic device.

The system may also include or be coupled to an imaging modality such as ultrasound, CT, fluoroscopy or MRI, overhead 3D stereotactic system (via pre-procedure MRI and/or CT). For example, imaging devices useful in coupling with the system described herein comprise without limitation Magnetic Resonance Imaging (MRI), functional Magnetic Resonance Imaging (fMRI), Magnetic Resonance Spectroscopy (MRS), diffusion MRI (DWI), diffusion tensor MRI (DTI), electroencephalography (EEG), magnetoencephalography (MEG), nuclear neuroimaging, positron emission tomography (PET), single photon emission computed tomography (SPECT), Ictal-Interictal SPECT Analysis by Statistical Parametric Mapping (ISAS), Computed Tomography (CT), x-ray, fluoroscopy, angiography, ultrasonography, transcranial magnetic stimulation (TMS), transcranial direct current stimulation (tDCS), transcranial electrical stimulation (TES), motor evoked potential (MEP), somatosensory evoked potential (SSEP), phase reversal of somatosensory evoked potential, evoked potential, electrocorticography (ECoG), direct cortical electrical stimulation (DCES), microelectrode recording (MER) or local field potential recording (LFP).

As described above, the system including the robotic device, the sensors of the robotic device, components of the intravenous assembly and their corresponding sensors can communicate through a wireless connection such as a Bluetooth® radio. The Bluetooth® radio of the robotic device can pair with the Bluetooth® radio of the component of the intravenous assembly so that data can be transmitted. It is contemplated that in addition to the robotic device and components of the intravenous assembly having a wireless connection such as a Bluetooth® radio, a personal computer used by the medical staff can also include a wireless connection so that the system can communicate to the personal computer. Examples of a personal computer include, but is not limited to network/stand-alone computers, personal digital assistants (PDAs), WebTV (or other Internet-only) terminals, set-top boxes, cellular/phones, screenphones, pagers, blackberry, smart phones, iPhone, iPad, table, peer/non-peer technologies, kiosks, or other known (wired or wireless) communication devices, etc.

The system can further include a software program that is associated with operation of the robotic device and/or a software program associated with a message digest with a date and time stamp that lists the various tasks performed by the robotic device on the components of the intravenous assembly. In some embodiments, information compiled from the message digest can be transmitted via Wi-Fi to a web dashboard on medical staff computers. The web dashboard can generate a report for the medical staff.

Dedicated hardware implementations, such as but not limited to ASICs (Application Specific Integrated Circuits), programmable logic arrays, and other hardware devices can likewise be constructed to implement the system described herein. Applications that include the system of various embodiments broadly comprise a variety of electronic and computer systems. Some embodiments implement functions in two or more specific interconnected hardware modules or devices with related control and data signals communicated between and through the modules, or as portions of an ASIC. Thus, the example system is applicable to software, firmware, and/or hardware implementations.

Data from the sensors of the components of the intravenous assembly may be downloaded in one or more textual/graphical formats (e.g., RTF, PDF, TIFF, JPEG, STL, XML, XDFL, TXT etc.), or set for alternative delivery to a smartphone and/or the web dashboard of a computer employed by medical staff.

The medical staff can interface with the computer (e.g., smartphone, a computer of the practitioner etc.) via a user interface that may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of the medical staff with the data from the sensors via the user interface. The user interface may be directly coupled to a database or directly coupled to a network server system via the Internet or cloud computing.

In some embodiments, the user interface device may be implemented as a graphical user interface (GUI) containing a display or the like, or may be a link to other user input/output devices known in the art. Individual or of a plurality of devices (e.g., network/stand-alone computers, personal digital assistants (PDAs), WebTV (or other Internet-only) terminals, set-top boxes, cellular/phones, screenphones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow medical staff to interface with the sensor data in the manner described. Database hardware and software can be developed for access by medical staff through personal computers, mainframes, and other processor-based devices. Medical staff may access the data stored locally on hard drives, CD-ROMs, stored on network storage devices through a local area network, or stored on remote database systems through one or more disparate network paths (e.g., the Internet).

The electronic circuitry in the robotic device, may include some or all of the capabilities of a computer in communication with a network and/or directly with other computers. The computer may include the processor as described above, a storage device, a display or other output device, an input device, and a network interface device, all connected via a bus. A battery can be provided to couple and power the computer. The computer may communicate with a network. The processor represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor executes instructions and includes that portion of the computer that controls the operation of the entire computer. The processor typically includes a control unit (the controller) that organizes data and program storage in memory and transfers data and other information between the various parts of the computer. The processor receives input data from the input device (e.g., the at least one sensor) and the network reads and stores instructions (for example processor executable code) and data in a main memory, such as random access memory (RAM), static memory, such as read only memory (ROM), and a storage device. The processor may also present data to a user via an output device or user interface, as described above, such as the screen of the smartphone or the monitor of the web dashboard of the medical staff's computer or a display is the robotic device is equipped with one.

Data can be stored in storage devices or systems (e.g., Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include a data storage device, a collection component for collecting information from users or other computers into centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against data storage device containing a variety of information collected by the collection device.

The disclosed system may be associated with a computer network-based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). For example, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., the at least one sensor or network of sensors of the robotic device and components of the intravenous assembly).

Components of the intravenous assembly, such as the sleeve used in conjunction with the intravenous tube, is reusable and washable. The system and its components can be made from various materials, such as, for example, plastic, such as a thermoplastic material. In some embodiments, materials include, but are not limited to thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy and their combinations.

The system and its components can also be made from materials such as, for example stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, for example GUM METAL®), ceramics and composites thereof for example calcium phosphate (e.g., SKELITE™), fabric, silicone, polyuret copolymers, polymeric rubbers, polyolefin rubbers, hydrogels, semi-rigid and rigid materials, elastomers.

The system and its components can also be made from materials such as, for example polyester (PES), polyethylene (PE), high-density polyethylene (HDPE), polyvinyl chloride (PVC), polyvinylidene chloride (PVDC) (Saran), low-density polyethylene (LDPE), polypropylene (PP), polystyrene (PS), high impact polystyrene (HIPS), polyamides (PA) (Nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), and/or polyurethanes (PU).

The system and its components, individually or collectively, may also be fabricated from a heterogeneous material for example a combination of two or more of the above-described materials.

Components of the intravenous assembly such as the sleeve used in conjunction with the intravenous tubing can be sterilized by radiation via terminal sterilization. Terminal sterilization of a product provides greater assurance of sterility than from processes such as an aseptic process, which requires individual product components to be sterilized separately and the final package assembled in a sterile environment.

Gamma radiation can also be used in the terminal sterilization step, which involves utilizing ionizing energy. Gamma rays are highly effective in killing microorganisms, they leave no residues, nor do they have sufficient energy to impart radioactivity to the spacer. Gamma rays can be employed when the spacer is in a package and gamma sterilization does not require high pressures or vacuum conditions, thus, package seals and other components are not stressed. In addition, gamma radiation eliminates the need for permeable packaging materials.

Electron beam (e-beam) radiation may also be used to sterilize one or more components of the intravenous assembly. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Robotic Device Operation

Figure 25:
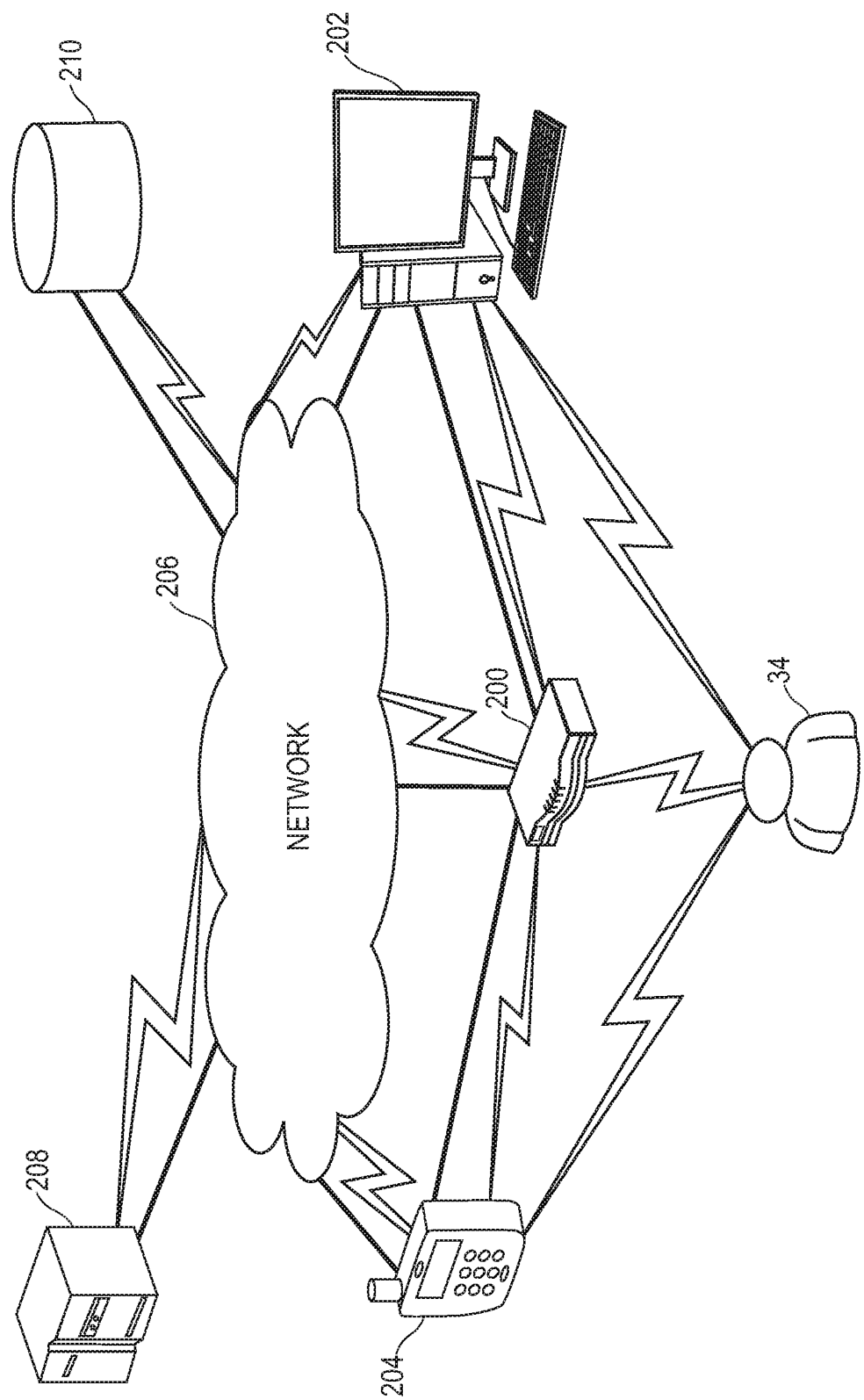
FIG. 25 is a block diagram of a system in which the robotic device is used to monitor and maintain the intravenous assembly, as well as collect, transfer, process, and store data obtained from the sensors.

FIG. 25 is a block diagram of a system in which the robotic device is used to monitor and maintain the intravenous assembly, as well as collect, transfer, process, and store data obtained from the sensors. The robotic device 34 can wirelessly transfer the data to, for example, a router 200, personal computer 202, phone 204, and/or any other electronic device capable of performing wireless transfers of the information. The router 200, personal computer 202, and/or phone 204 can then further transfer this data to and/or from the router 200, personal computer 202, phone 204, and/or network 206 using wired and/or wireless techniques. This information may be further processed and/or stored via the network 206 by using, for example, the personal computer 202, server 208, and/or database 210. Each of the router 200, phone 204, personal computer 202, network 206 may include capability to receive and/or transmit information from and/or to any other device using wired and/or wireless techniques and/or protocols, such as but not limited to, Bluetooth, Wi-Fi, radio frequency, optical, and/or any other type of wireless communication linkage. The network 206 may be any type of network including, but not limited to, a wide area network, local area network, and/or telephone network.

Figure 26:
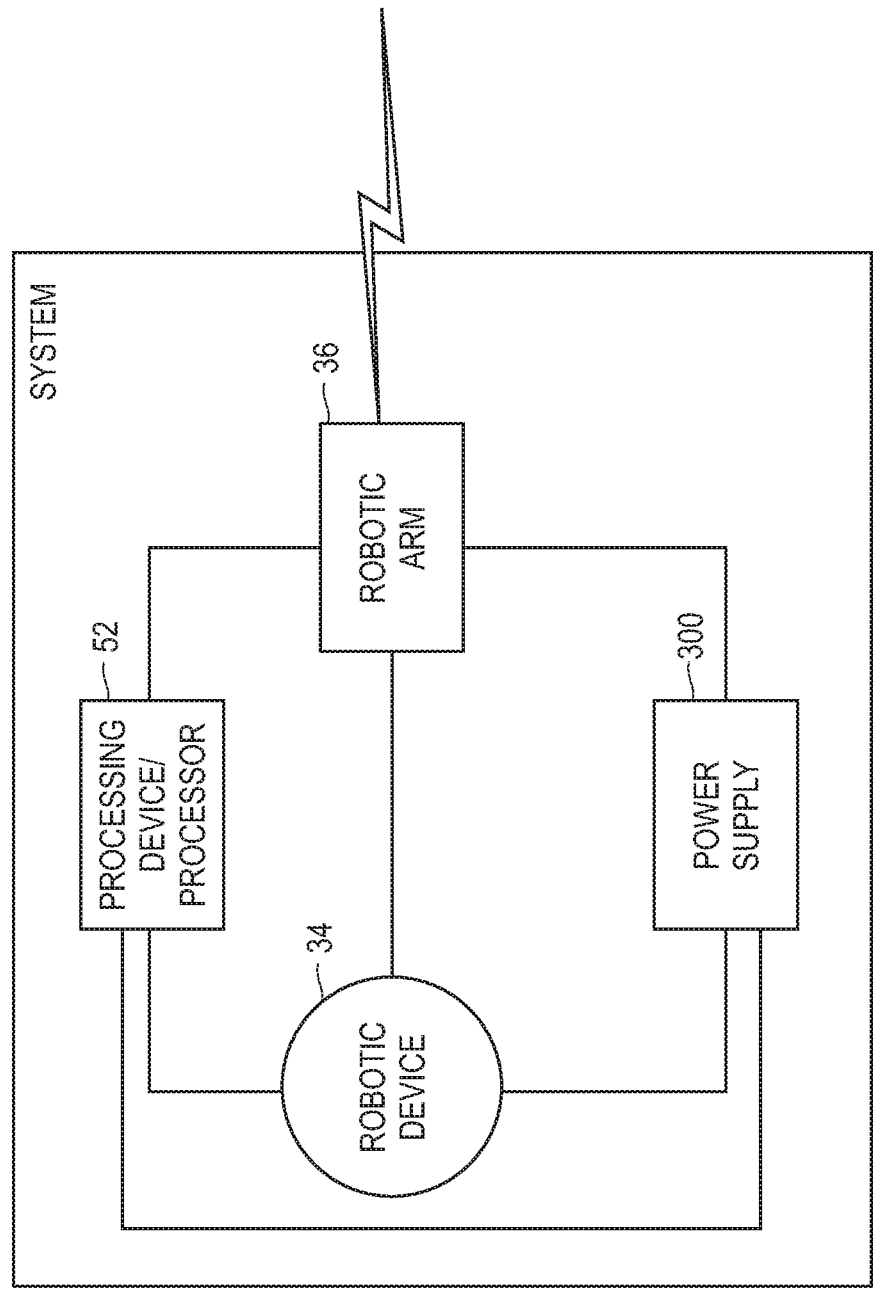
FIG. 26 is a block diagram of the system that monitors information associated with the intravenous assembly, the system comprising the robotic device including the optical and pressure sensors, the robotic arm coupled to the robotic device, a processing device and a power supply.

FIG. 26 is a block diagram of the system. The system can include the robotic device 34, the robotic arm 36, the processor or processing device 52, and a power supply 300 operatively coupled together using unidirectional and/or bidirectional connections. The robotic device 34 includes the optical and pressure sensors described above designed to monitor errant flow through physical, chemical, biological, and/or environmental information associated with the intravenous assembly, and provide this information to the processor 52 and/or robotic arm 36. The processor 52 may perform further processing on the information obtained from the robotic device 34, and provide the processed information to the robotic arm 36. The robotic device 34 is able to wirelessly transfer data between the robotic device 34 and devices external to the robotic device, such as the router 200, phone 204, and personal computer 202, and network 206 shown in FIG. 25. The power supply 300 provides power to the robotic device, robotic arm 36, and processor 52.

The system may also include a computer-readable storage device (not shown) operatively coupled to at least one of the robotic device 34, processor 52, and/or robotic arm 36. The computer-readable storage device is configured to store data provided by the robotic device 34, robotic arm 36, and/or processor 52 for subsequent retrieval and/or transmission. The computer-readable storage device may include, for example, Flash memory, RAM, ROM, EEPROM, or any other computer-readable storage medium which can be used to store information.

Figure 27:
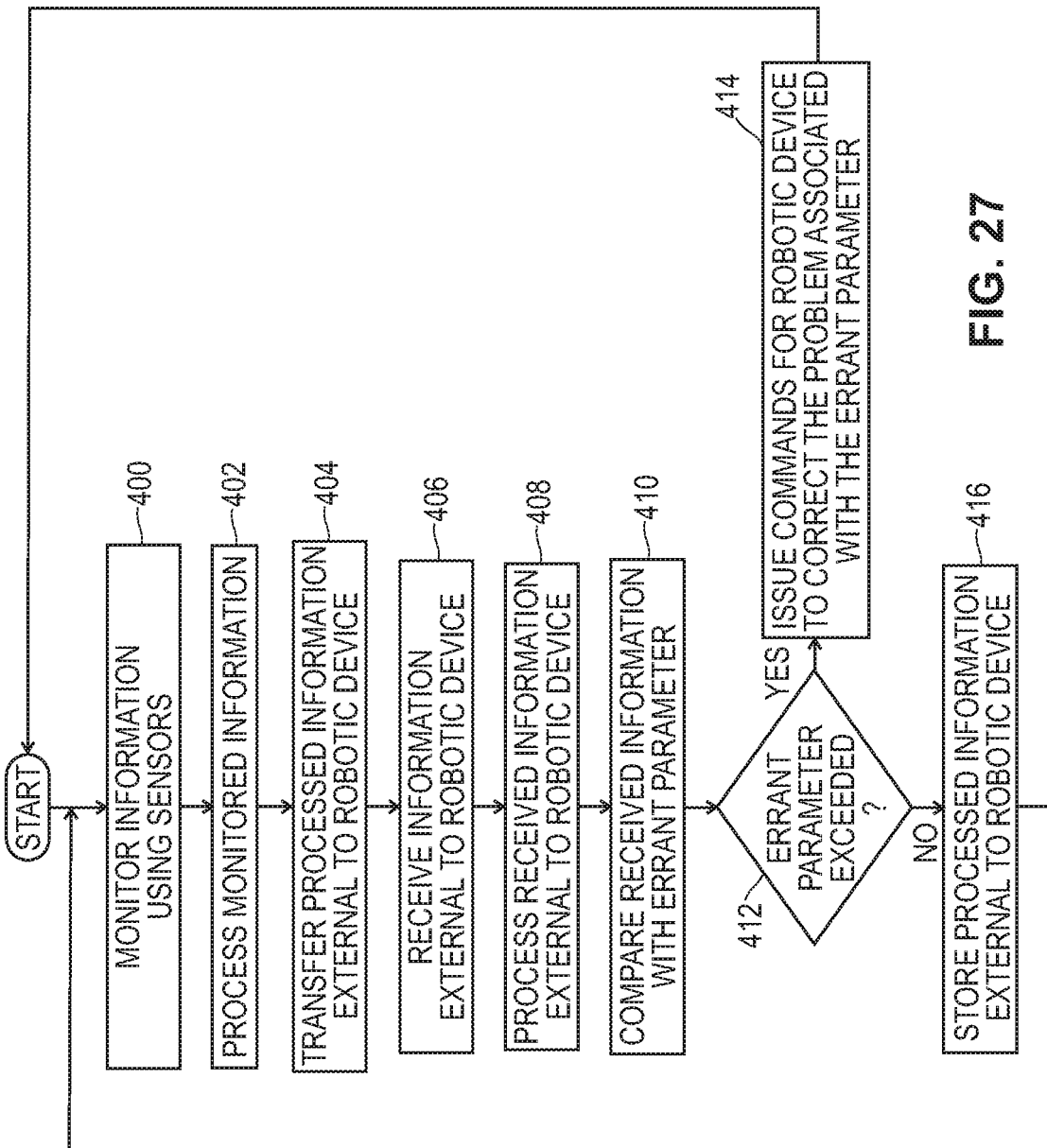
FIG. 27 is a flow chart illustrating the logic executed by the system when errant flow is detected by the sensors of the intravenous assembly. Information is monitored using one or more sensors in the intravenous assembly and the sensors of the robotic device, and the monitored information is optionally processed by the processor. The optionally processed information is transferred external to the robotic device and the transferred information is received by one or more devices external to the robotic device. The received information is processed by one or more devices external to the robotic device. Information received is then compared with errant parameters. A query of whether an errant parameter has been exceeded is prompted. If the errant parameter is exceeded, then commands are issued for the robotic device to correct the problem associated with the errant parameter. If the errant parameter is not exceeded, then the processed information is stored external to the robotic device for future access.

FIG. 27 is a flow chart illustrating the logic executed by the system when errant flow is detected by the sensors of the intravenous assembly. Information is monitored using one or more sensors in the intravenous assembly (e.g., the intravenous tubing, intravenous catheter, intravenous container and/or intravenous pump) and the sensors of the robotic device such as the pressure sensor and the optical sensor in step 400, and the monitored information is optionally processed by the processor in step 402. The optionally processed information is transferred external to the robotic device by for example, a wireless connection in step 404, and the transferred information is received by one or more devices external to the robotic device in step 406. The received information is processed by one or more devices external to the robotic device in step 408. Information received is then compared with errant parameters associated with high pressure or low pressure, air bubbles, occlusions, clots, and/or kinks in an intravenous assembly such as intravenous tubing in step 410. A query of whether an errant parameter has been exceeded in step 412 is prompted. If the errant parameter is exceeded, then commands are issued for the robotic device to correct the problem associated with the errant parameter in step 414. If the errant parameter is not exceeded, then the processed information is stored external to the robotic device for future access in step 416. It is to be understood that the robotic device can correct the problem associated with an errant parameter before an alarm is triggered in the intravenous pump.

Figure 28:
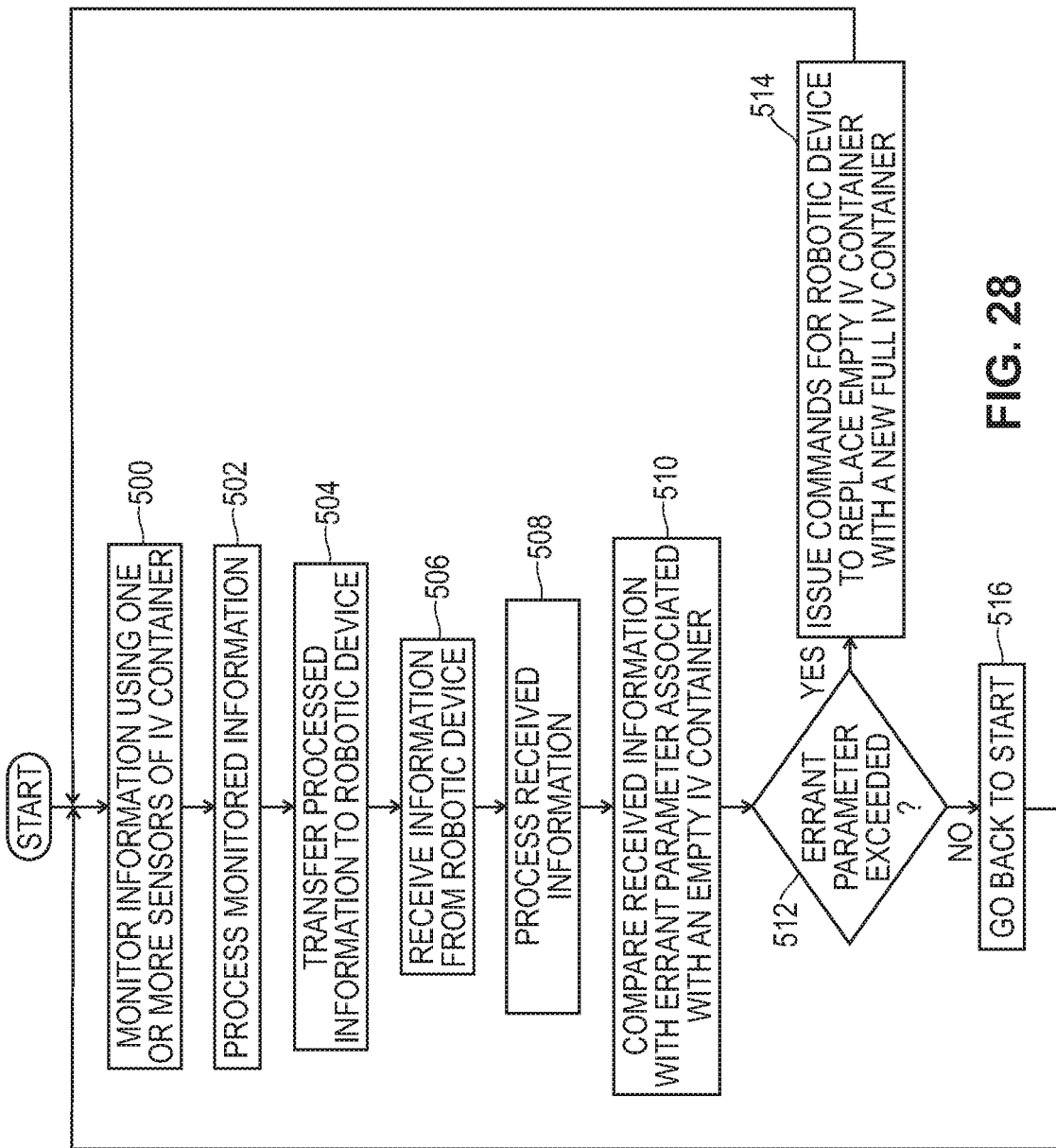
FIG. 28 is a flowchart of the logic executed by the robotic device when prompted to change an intravenous container when it is empty. Information is monitored using one or more sensors of the intravenous container, and the monitored information is optionally processed and transferred. The transferred information is received by the robotic device and the received information is processed. Information received is then compared with errant parameters associated with an empty intravenous container. A query of whether an errant parameter has been exceeded is prompted. If the errant parameter has been exceeded, then commands are issued for the robotic device to replace the empty intravenous container with a new full intravenous container. If the errant parameter is not exceeded, then a command is issued to "go back to start" to start over.

FIG. 28 is a flow chart illustrating the logic executed by the robotic device when prompted to change an intravenous container that is empty. Information is monitored using one or more sensors of the intravenous container in step 500, and the monitored information is optionally processed and transferred in steps 502 and 504 respectively. The transferred information is received by the robotic device in step 506 and the received information is processed in step 508. Information received is then compared with errant parameters associated with an empty intravenous container in step 510. A query of whether an errant parameter has been exceeded in step 512 is prompted. If the errant parameter is exceeded, then commands are issued for the robotic device to replace the empty intravenous container with a new full intravenous container in step 514. If the errant parameter is not exceeded, then a command is issued to "go back to start" to start over in step 516.

Figure 29:
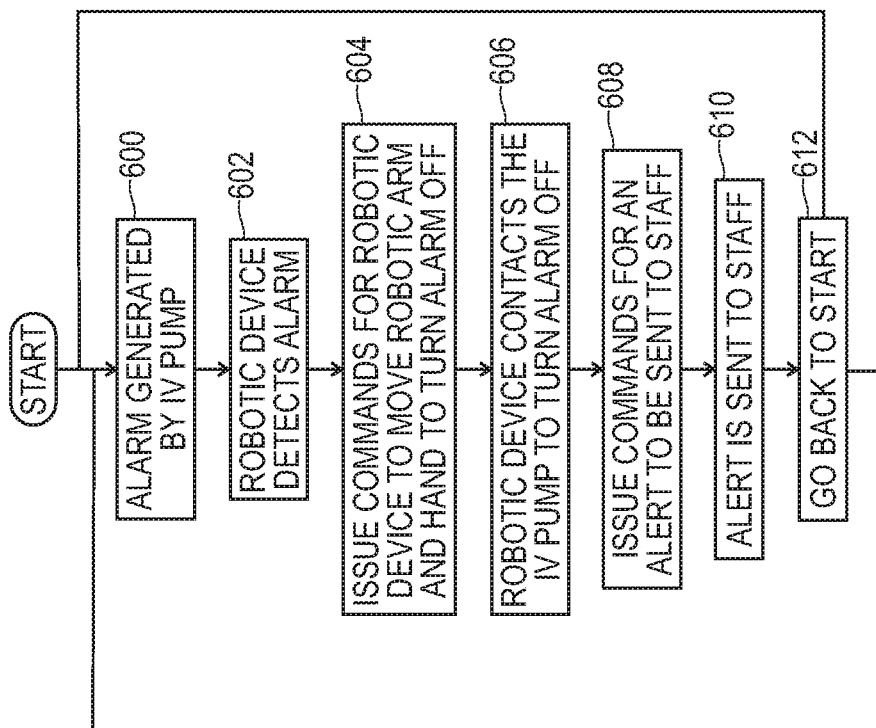
FIG. 29 is a flowchart illustrating logic steps associated with the robotic device when an alarm is generated by the intravenous pump. An alarm is generated by the intravenous pump. The robotic device detects the alarm through a sensor such as an optical or a sound sensor. Commands are issued by the processor for the robotic device to move its arm and hand which are moved by the controller to turn the alarm off. The robotic device moves and contacts the intravenous pump and turns the alarm off. A command is then issued for an alert to be sent to medical staff and the alert is then sent alerting the medical staff that the alarm has been successfully turned off. A command is then issued to "go back to start".

FIG. 29 is a flowchart illustrating logic steps associated with the robotic device when an alarm is generated by the intravenous pump. An alarm is generated by the intravenous pump in step 600. The robotic device detects the alarm through a sensor such as an optical or a sound sensor in step 602. Commands are issued by the processor for the robotic device to move its arm and hand which are moved by the controller to turn the alarm off in step 604. The robotic device moves and contacts the intravenous pump and turns the alarm off in step 606. A command is then issued for an alert to be sent to medical staff in step 608 and the alert is then sent alerting the medical staff that the alarm has been successfully turned off in step 610. A command is then issued to "go back to start" in step 612.

The term "processor" as used herein is intended to include any processor, such as, for example, one that includes a CPU (central processing unit) and/or other forms of processing circuitry. Further, the term "processor" may refer to more than one individual processor.

The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s) 412, input device(s) 414, cursor control device(s) 416, signal generation device(s) 420, etc., can be collectively referred to as an "input/output interface," and is intended to include one or more mechanisms for inputting data to the processing device (s), and one or more mechanisms for providing results associated with the processing device(s). Input/output or I/O devices including but not limited to keyboards (e.g., alphanumeric input device(s), display device(s), and the like) can be coupled to the system either directly (such as via bus) or through intervening input/output controllers (omitted for clarity).

In an integrated circuit implementation of one or more embodiments of the disclosure, multiple identical die are typically fabricated in a repeated pattern on a surface of a semiconductor wafer. Each such die may include a device described herein, and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this specification.

An integrated circuit in accordance with the embodiments of the disclosed embodiments can be employed in essentially any application and/or electronic system in which buffers are utilized. Suitable systems for implementing one or more embodiments of the disclosed embodiments include, but are not limited to, personal computers, interface devices (e.g., interface networks, high-speed memory interfaces (e.g., DDR3, DDR4), etc.), data storage systems (e.g., RAID system), data servers, etc. Systems incorporating such integrated circuits are considered part of the disclosed embodiments. Given the teachings provided herein, one of ordinary skill in the art will be able to contemplate other implementations and applications.

In accordance with various embodiments, the methods, functions or logic described herein are implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

It should also be noted that software, which implements the methods, functions and/or logic herein, are optionally stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

Medicaments

Various medicaments (e.g., medications) can be administered through the intravenous assembly described above. For example, these medicaments include, but are not limited to Abatacept, Acetaminophen, Acetazolamide, Acetylcysteine, Acyclovir, Adenosine, Albumin, Aldesleukin, Alemtuzumab, Alfentanil, Alphal-Proteinase Inhibitor, Alprostadil, Alteplase, Amikacin Sulfate, Aminocaproic Acid, Aminophylline, Amiodarone, Amobarbital, Amphotericin B, Amphotericin B Lipid Complex (Abelcet®), Amphotericin B Liposomal (AmBisome®), Ampicillin Sodium, Ampicillin/sulbactam (Unasyn®), Antihemophilic Factor, VI, Antihemophilic Factor IX, Recombinant, Antihemophilic Factor VIII, Monoclonal, Antihemophilic Factor VIII, Recombinant, Antithrombin III, Antivenin, Lactrodectus *mactans*, Aprotinin, Arginine, Arsenic Trioxide, Ascorbic Acid, Atracurium Besylate, Atropine Sulfate, Azathioprine, Azacitidine, Azithromycin, Aztreonam, Basiliximab, Belimumab, Bendamustine, Benztropine, Bevacizumab, Bivalirudin, Bleomycin Sulfate, Bortezomib, Bumetanide, Busulfan, Benzoate, Calcium Gluconate, Carboplatin, Carfilzomib, Carmustine, Cefotaxime, Ceftaroline, Ceftazidime, Ceftriaxone, Cefuroxime, Cetuximab, Chloramphenicol, Chlorothiazide, Cidofovir, Ciprofloxacin, Cisplatin, Cladribine, Clofarabine, Colistimethate, Cosyntropin, Cyclophosphamide, Cyclosporine, Cytarabine, Cytomegalovirus immune globulin, or a combination thereof.

The medicaments can also include, but are not limited to Dacarbazine, Daclizumab, Dactinomycin, Daptomycin, Daratumumab, Daunorubicin, Deferoxamine, Desmopressin, Dexamethasone, Dexmedetomidine, Dexrazoxane, Digoxin, Dihydroergotamine Mesylate, Docetaxel, Dopamine, Doxorubicin, Doxycycline, Droperidol, Edrophonium Chloride, Ephedrine, Ethacrynic acid, Etomidate, Etoposide, Fat Emulsion 20%, Fenoldopam, Fentanyl Citrate, Ferric Sodium Gluconate, Fluconazole, Fludarabine, Flumazenil, Fluorouracil, Folic Acid, Ganciclovir, Gemcitabine, Glucagon, Glucarpidase, Granisetron, Haloperidol Lactate, Heparin, Hydroxyzine, Immune Globulin (WIG), Indigotindisulfonate Sodium, insulin, Interferon Alfa-2B, Ipilimumab, Irinotecan, Iron Dextran, Iron Sucrose, Isavuconazonium sulfate (isavuconazole), Isoproterenol, Ketamine, Ketorolac, Labetalol, Leucovorin Calcium, Levetiracetam, Levothyroxine, Lorazepam, Magnesium Sulfate, Mannitol, Mechlorethamine, Melphalan, Meperidine, Methadone, Methotrexate, Methylene Blue, Micafungin, Mitomycin, Morphine, Naloxone, Nitroglycerin, Norepinephrine, Obinutuzumab, Octreotide, Oxacillin, Oxytocin, Paclitaxel, Pamidronate, Papaverine, Pegaspargase, Penicillin G Potassium, Pentamidine, Pentostatin, Phenobarbital, Phenylephrine, Phosphate (Potassium), Phosphate (Sodium), Phytonadione (Vitamin K), Piperacillin/tazobactam, Potassium Acetate, Potassium Chloride, Potassium Phosphate, Propranolol, Pyridoxine, Quinidine Gluconate, Ranitidine, Remifentanil, Rho D Immune Globulin, Rifampin, Sargramostim, Secretin, Sodium Acetate, Sodium Bicarbonate, Sodium Chloride 1.8%, Sodium Chloride 3%, Sodium Phosphate, Tacrolimus, Telavancin, Thiamine, Tigecycline, Tobramycin, Tromethamine, Vancomycin, Verapamil, Zinc trace metal, Zidovudine, Zoledronic Acid or a combination thereof.

Intravenous fluids can also be administered by the intravenous assembly described above. Intravenous fluids include, but are not limited to dextrose solutions such as 2.5%, 5%, 20% and 50% dextrose, sodium chloride solutions such as 5% NaCl (hypertonic), 3% NaCl (hypertonic), 0.9% NaCl (isotonic), 0.45% NaCl (hypotonic), 0.2% NaCl (hypotonic), sodium chloride solutions with dextrose such as 2.5% dextrose/0.45% NaCl (hypotonic), 5% dextrose/0.9% NaCl (isotonic), 5% dextrose/0.45% NaCl (isotonic) 5% dextrose/0.9% NaCl (hypertonic), and multiple electrolyte solutions such as Ringers solution, Lactated Ringer's, Normosol R and Plasma-Lyte M that are either isotonic, hypotonic or hypertonic solutions.

The illustrations of embodiments of the disclosure described herein are intended to provide a general understanding of the structure of various embodiments, and they are not intended to serve as a complete description of all the elements and features of devices and systems that might make use of the structures described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments are referred to herein, individually and/or collectively, by the terms "embodiment," "may include," "can include" or "it is contemplated" merely for convenience and without intending to limit the scope of this application to any single embodiment or concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, disclosed subject matter lies in less than all features of a single embodiment. Thus, the following claims are hereby incorporated into the Detailed Description, with each claim standing on its own as a separate example embodiment.

Given the teachings of the disclosure provided herein, one of ordinary skill in the art will be able to contemplate other implementations and applications of the techniques of the disclosure. Although illustrative embodiments of the disclosure have been described herein with reference to the accompanying drawings, it is to be understood that the disclosure is not limited to those precise embodiments, and that various other changes and modifications are made therein by one skilled in the art without departing from the scope of the appended claims.

While particular embodiments of the present disclosure have been shown and described, it will be appreciated by those skilled in the art that, based upon the teachings herein, changes and modifications may be made without departing from this disclosure and its broader aspects and, therefore, the appended claims are to encompass within their scope all such changes and modifications as are within the true spirit and scope of this disclosure.

Applications to Covid-19 Disease Diagnosis

According to a further aspect of this disclosure, the robotic device is configured to facilitate diagnosis of conditions indicating potential or actual Covid-19 disease. With reference to FIG. 4, for example, in this aspect the effector is positioned around the tubing (or even the patient's finger) to facilitate a type of pulse-oximetry measurement. In this embodiment element 38 is a light source (e.g., a pair of light emitting diodes (LEDs)), and element 40 is a photodetector (e.g., a photodiode). For example, one LED is red with a wavelength of 660 nanometers, while the other LED is infrared with a wavelength of 940 nanometers. Oxygenated hemoglobin absorbs more infrared light and allows more red light to pass through, whereas deoxygenated hemoglobin allows more infrared light to pass through and absorbs more red light. In operation, the LEDs are sequenced, and the photodiode receives the transmitted light. Using known signal processing (provided by the processor) based on the ratio of the red light measurement to the infrared light measurement, the oximeter determines the percentage of blood that is loaded with oxygen. Upon an indication of an oxygen deficiency or anomaly as measured by the oximeter, a notification (e.g., an alert) is provided to medical staff or other interested persons (including the patient). In this manner, the robot is used to indirectly monitor oxygen saturation in the patient's blood, thereby providing an accurate and safe indication of an underlying condition indicative of potential Covid-19 disease.

In an alternative embodiment, the robot arm that carries appropriate sensors and detectors is commanded into position, e.g., to grasp a finger of a patient, and controlled using those sensors and detectors (and associated processor support and software) to noninvasively detect molecules indicative of the SARS-Cov-2 virus or its antibodies. Thus, and once again with reference to FIG. 4, element 38 is an interferometer. One example would be a bimodal waveguide interferometer, which is a device that uses two modes of a light beam traveling in a single waveguide. Element 40 is a photodetector, which records the interference between the light modes as the light passes through the bodily fluid. By processing the signals generating by the photodetector, relevant molecules (or their absence) is detected. The biosensor results are then output to medical staff or other interested persons or entities.

Biosensors carried by the robot are not limited to those that use light. Every protein or molecule has its unique electrical charge, light absorption, and magnetic force. Depending on the nature of the testing, the biosensor can also be one that detects unique electrical charge, or magnetic force, or combinations of any of the above.

The true spirit and scope is considered to encompass devices and processes, unless specifically limited to distinguish from known subject matter, which provide equivalent functions as required for interaction with other elements of the claims and the scope is not considered limited to devices and functions currently in existence where future developments may supplant usage of currently available devices and processes yet provide the functioning required for interaction with other claim elements. Furthermore, it is to be understood that the disclosure is solely defined by the appended claims.

The invention claimed is:

1. A method to monitor and autonomously configure an intravascular assembly without medical staff involvement or presence, comprising:

associating a robotic device with an intravascular assembly, the intravascular assembly having tubing through which fluids are delivered intravenously;

continuously monitoring the tubing;

responsive to the monitoring, detecting an errant flow through the tubing that results from one of: a kink or twist in the tubing, an air bubble in the tubing, an occlusion or clot in the tubing, and pressure variations; and responsive to detecting the errant flow, and in advance of an audible alarm being generated in association with the intravascular assembly, issuing a command to the associated robotic device, the command configured to initiate, by the robotic device, engagement with and mechanical manipulation of the tubing, thereby remediating the errant flow before the audible alarm occurs, wherein the audible alarm is triggerable due to the errant flow.

2. The method as described in claim 1 wherein the errant flow is detected by a sensor carried on the robotic device.

3. The method as described in claim 1 wherein the errant flow is detected by one or more sensors located with the tubing.

4. The method as described in claim 1 wherein the command is issued to the associated robotic device wirelessly.

5. The method as described in claim 1 further including:
   deactivating the audible alarm at the intravascular assembly; and
   silently issuing an alert that the audible alarm has been deactivated but that the errant flow has been remediated.

6. The method as described in claim 1 wherein the mechanical manipulation engages the tubing and unkinks or untwists the tubing to remediate the errant flow.

7. The method as described in claim 1 wherein the monitoring is performed by the robotic device.

8. The method as described in claim 1 further including processing information associated with the detected errant flow and, responsive to the processing, issuing the command.

9. The method as described in claim 1 further including:
   configuring an oximeter on the robotic device; and
   indirectly monitoring oxygen saturation using the robotic device; and
   responsive to a monitored oxygen saturation, issuing a notification of a medical condition indicating a potential Covid-19 disease.

10. A method to monitor and autonomously configure an intravascular assembly without medical staff involvement or presence, comprising:
    associating a robotic device with an intravascular assembly, the intravascular assembly having tubing through which fluids are delivered intravenously;
    continuously monitoring the tubing;
    responsive to the monitoring, detecting an errant flow through the tubing that results from one of: a kink or twist in the tubing, an air bubble in the tubing, an occlusion or clot in the tubing, and pressure variations; and
    responsive to detecting the errant flow, and in advance of an audible alarm being generated in association with the intravascular assembly, issuing a command to the associated robotic device, the command configured to initiate, by the robotic device, engagement with and mechanical manipulation of the tubing, thereby remediating the errant flow, wherein the robotic device comprises a robotic hand that unkinks or untwists the tubing by moving over one or more attachment points or a track surrounding the tubing, and wherein the mechanical manipulation engages the tubing and unkinks or untwists the tubing to remediate the errant flow.

11. A method to monitor and autonomously configure an intravascular assembly without medical staff involvement or presence, comprising:
    associating a robotic device with an intravascular assembly, the intravascular assembly having tubing through which fluids are delivered intravenously;
    continuously monitoring the tubing;
    responsive to the monitoring, detecting an errant flow through the tubing that results from one of: a kink or twist in the tubing, an air bubble in the tubing, an occlusion or clot in the tubing, and pressure variations;
    responsive to detecting the errant flow, and in advance of an audible alarm being generated in association with the intravascular assembly, issuing a command to the associated robotic device, the command configured to initiate, by the robotic device, engagement with and mechanical manipulation of the tubing, thereby remediating the errant flow;
    configuring a biosensor on the robotic device;
    collecting information generated by the biosensor; and
    responsive to a determination that the information indicates presence or absence of SARS-Cov-2 virus or antibodies of SARS-Cov-2 virus, outputting the information to other persons or entities.

\* \* \* \* \*